US005728555A

United States Patent [19]

Fotheringham et al.

[11] Patent Number: 5,728,555
[45] Date of Patent: Mar. 17, 1998

[54] PREPARATION OF D-AMINO ACIDS BY DIRECT FERMENTATIVE MEANS

[75] Inventors: Ian G. Fotheringham, Vernon Hills; Paul P. Taylor, Arlington Heights; Jennifer L. Ton, Palatine, all of Ill.

[73] Assignee: Monsanto Company, St. Louis, Mo.

[21] Appl. No.: 723,896

[22] Filed: Sep. 30, 1996

[51] Int. Cl.$^6$ ............ C12P 13/04; C12P 13/20; C12P 13/22; C12N 1/20

[52] U.S. Cl. ............ 435/106; 435/107; 435/108; 435/109; 435/110; 435/113; 435/114; 435/115; 435/116; 435/252.3; 435/252.31

[58] Field of Search ............ 435/106, 107, 435/108, 109, 110, 111, 113, 114, 115, 116, 252.3–252.35

[56] References Cited

U.S. PATENT DOCUMENTS

| | | | |
|---|---|---|---|
| 4,753,883 | 6/1988 | Backman et al. | 435/232 |
| 5,120,837 | 6/1992 | Fotheringham et al. | 536/27 |
| 5,354,672 | 10/1994 | Fotheringham | 435/106 |
| 5,559,016 | 9/1996 | Katsumata et al. | 435/116 |

FOREIGN PATENT DOCUMENTS

WO 9105870  5/1991  European Pat. Off. .

OTHER PUBLICATIONS

Christen, et al, "Transaminases," 1985, 464.

Drechsel et al., "α-Keto Acids Are Novel Siderophores in the Genera *Proteus, Providencia,* and *Morganella* and Are Produced by Amino Acid Deaminases," Journal of Bacteriology, vol. 175, No. 9, 1993, 2727.

Jones et al., "D–Glutamate–D–Amino Acid Transaminase from Bacteria," Methods in Enzymology, vol. 113, 1985, 108.

Lugtenberg et al, "Properties of a D–Glutamic Acid–Requiring Mutant of *Escherichia coli,*" vol. 114, No. 2, Journal of Bacteriology, 1973, 499.

Massad et al., "*Proteus mirabilis* Amino Acid Deaminase: Cloning, Nucleotide Sequence, and Characterization of aad," vol. 177, No. 20, Journal of Bacteriology, 1995, 5878.

Pucci et al., "*Staphylococcus haemolyticus* Contains Two D–Glutamic Acid Biosynthetic Activities, a Glutamate Racemase and a D–Amino Acid Transaminase," vol. 177, No. 2, Journal of Bacteriology, 1995, 336.

Stoddard et al., "Preliminary X–ray Data for a D–Amino Acid Amino–transferase from a Novel Thermophilic *Bacillus,*" vol. 196, No. 2, Journal of Molecular Biology, 1987, 441.

Tanizawa, et al., "Thermostable D–Amino Acid Aminotransferase from a Thermophilic *Bacillus* Species," vol. 264, No. 5, The Journal of Biological Chemistry, 1989, 2445.

Tanizawa et al., "The Primary Structure of Thermostable D–Amino Acid Aminotransferase from a Thermophilic Bacillus Species and Its Correlation withh L–Amino Acid Amintransferases," vol. 264, No. 5, The Journal of Biological Chemistry, 1989, 2450.

*Primary Examiner*—Robert A. Wax
*Assistant Examiner*—Einar Stole
*Attorney, Agent, or Firm*—Fitzpatrick, Cella, Harper & Scinto

[57] ABSTRACT

The present invention relates to materials and methods for production of natural and unnatural D-amino acids. In particular, the present invention relates to a fermentation method for the production of D-amino acids using recombinant host cells.

Specifically, the invention relates to a method for producing a D-amino acid in a cell, comprising:

(a) incorporating into the cell a D-aminotransferase gene and a L-aminodeaminase gene;
(b) culturing the cell in a cell culture medium; and
(c) isolating the D-amino acid from the cell culture medium.

The invention also relates to a method for producing D-phenylalanine in a cell, comprising:

(a) incorporating into the cell a D-aminotransferase gene, a L-aminodeaminase gene and means for increasing production of phenylpyruvate;
(b) culturing the cell in a cell culture medium; and
(c) isolating the D-phenylalanine from the cell culture medium.

The invention also relates to the preparation of recombinant cells for use in the production of enantiomerically pure D-amino acids.

50 Claims, 13 Drawing Sheets

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
( A ) LENGTH: 95 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
AAGCTTTTTT  GTTGACAGCG  TGAAAACAGT  ACGGGTATAA  TACTAAAGTC  ACAAGGAGGA        60

TCCACTATGA  CATCGGAAAA  CCCGTTACTG  GCGCT                                     95
```

( 2 ) INFORMATION FOR SEQ ID NO:2:

( i ) SEQUENCE CHARACTERISTICS:
( A ) LENGTH: 1424 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 427..1275

( x i ) SEQUENCE DESCRIPTION: SEQ ID NO:2:

```
ACAAGGAGGA  TCCGTTAATC  CAAACGTTAG  CTGGTGTTTA  TCGCCGACAA  ACGGGCGATA        60

ACGAAACACC  TTTACTTTCA  ACAGGCGGTG  GAACGTATGC  ACGCGTCTTG  AAAAAGGTG        120

TGGCATTCGG  CATGCTTTTC  CCTGGTGATC  CAGATGTCAT  GCATCGTGCG  GATGAATATG       180

TAATTGTTGA  TAAATTAGTA  CAAGCTGCTG  CTATTTATGC  AGAAGCCATT  GCAGAACTGG       240

CTGGGAAGTA  AGTGTCATTA  AGAGCGTAAT  GTTTCTTGC   CAAAGAGATC  ACGAAGCTTC      300

ACACGCCAAG  CACTTCACTG  AAAAATCTAC  TTTGATTTAC  TGCATCTGGT  CTTACTTGAT      360

CGTCTAGTGG  GAATCATTGT  ACTTAAAAAT  GTGAAAATAA  CTTAAAAATG  AAAAGGATGT      420
```

```
ATAAAC  ATG  GCA  TAC  TCA  TTA  TGG  AAT  GAC  CAA  ATC  GTT  GAA  GAA  GGA        468
        Met  Ala  Tyr  Ser  Leu  Trp  Asn  Asp  Gln  Ile  Val  Glu  Glu  Gly
          1                    5                        10

TCT  ATT  ACA  ATT  TCA  CCA  GAA  GAC  CGT  GGT  TAT  CAA  TTT  GGT  GAT  GGT        516
Ser  Ile  Thr  Ile  Ser  Pro  Glu  Asp  Arg  Gly  Tyr  Gln  Phe  Gly  Asp  Gly
 15                    20                        25                         30

ATT  TAC  GAA  GTA  ATC  AAA  GTA  TAT  AAC  GGG  CAT  ATG  TTT  ACA  GCA  CAA        564
Ile  Tyr  Glu  Val  Ile  Lys  Val  Tyr  Asn  Gly  His  Met  Phe  Thr  Ala  Gln
                         35                        40                         45

GAG  CAC  ATC  GAT  GCT  TTC  TAT  GCT  AGT  GCC  GAA  AAA  ATT  CGC  CTT  GTT        612
Glu  His  Ile  Asp  Ala  Phe  Tyr  Ala  Ser  Ala  Glu  Lys  Ile  Arg  Leu  Val
                 50                        55                         60

ATT  CCT  TAT  ACA  AAA  GAT  GTA  TTA  CAC  AAA  TTA  TTG  CAT  GAT  TTA  ATC        660
Ile  Pro  Tyr  Thr  Lys  Asp  Val  Leu  His  Lys  Leu  Leu  His  Asp  Leu  Ile
             65                        70                         75

GAA  AAA  AAT  AAT  TTA  AAT  ACA  GGT  CAT  GTT  TAC  TTC  CAA  ATT  ACA  CGT        708
Glu  Lys  Asn  Asn  Leu  Asn  Thr  Gly  His  Val  Tyr  Phe  Gln  Ile  Thr  Arg
         80                        85                         90

GGA  ACA  ACT  TCT  CGT  AAC  CAC  ATT  TTC  CCG  GAT  GCA  AGC  GTA  CCA  GCA        756
```

| | | | | | | | | | | | | | | | | |
|---|---|---|---|---|---|---|---|---|---|---|---|---|---|---|---|---|
| Gly | Thr | Thr | Ser | Arg | Asn | His | Ile | Phe | Pro | Asp | Ala | Ser | Val | Pro | Ala | |
| 95 | | | | | 100 | | | | 105 | | | | | | 110 | |

| GTG | CTA | ACA | GGT | AAT | GTT | AAA | ACT | GGT | GAA | CGT | TCA | ATT | GAA | AAT | TTC | 804 |
|---|---|---|---|---|---|---|---|---|---|---|---|---|---|---|---|---|
| Val | Leu | Thr | Gly | Asn | Val | Lys | Thr | Gly | Glu | Arg | Ser | Ile | Glu | Asn | Phe | |
| | | | | 115 | | | | 120 | | | | | | 125 | | |

| GAA | AAA | GGC | GTA | AAA | GCG | ACA | TTG | GTT | GAA | GAT | GTT | CGT | TGG | TTA | CGT | 852 |
|---|---|---|---|---|---|---|---|---|---|---|---|---|---|---|---|---|
| Glu | Lys | Gly | Val | Lys | Ala | Thr | Leu | Val | Glu | Asp | Val | Arg | Trp | Leu | Arg | |
| | | | 130 | | | | | 135 | | | | | 140 | | | |

| TGT | GAT | ATT | AAA | TCT | TTA | AAT | TTA | CTT | GGC | GCG | GTA | CTT | GCG | AAA | CAA | 900 |
|---|---|---|---|---|---|---|---|---|---|---|---|---|---|---|---|---|
| Cys | Asp | Ile | Lys | Ser | Leu | Asn | Leu | Leu | Gly | Ala | Val | Leu | Ala | Lys | Gln | |
| | | | 145 | | | | 150 | | | | | 155 | | | | |

| GAA | GCA | TCT | GAA | AAA | GGT | TGT | TAC | GAA | GCC | ATT | TTA | CAC | CGT | GGA | GAT | 948 |
|---|---|---|---|---|---|---|---|---|---|---|---|---|---|---|---|---|
| Glu | Ala | Ser | Glu | Lys | Gly | Cys | Tyr | Glu | Ala | Ile | Leu | His | Arg | Gly | Asp | |
| | | 160 | | | | | 165 | | | | | 170 | | | | |

| ATT | ATC | ACA | GAA | TGT | TCT | TCT | GCT | AAT | GTC | TAT | GGT | ATT | AAA | GAT | GGT | 996 |
|---|---|---|---|---|---|---|---|---|---|---|---|---|---|---|---|---|
| Ile | Ile | Thr | Glu | Cys | Ser | Ser | Ala | Asn | Val | Tyr | Gly | Ile | Lys | Asp | Gly | |
| 175 | | | | | 180 | | | | | 185 | | | | | 190 | |

| AAA | CTT | TAT | ACG | CAC | CCA | GCA | AAT | AAC | TAC | ATC | TTA | AAT | GGT | ATT | ACA | 1044 |
|---|---|---|---|---|---|---|---|---|---|---|---|---|---|---|---|---|
| Lys | Leu | Tyr | Thr | His | Pro | Ala | Asn | Asn | Tyr | Ile | Leu | Asn | Gly | Ile | Thr | |
| | | | | 195 | | | | | 200 | | | | | 205 | | |

| CGC | CAA | GTT | ATA | TTA | AAA | TGT | GCC | GCT | GAA | ATA | AAT | TTA | CCA | GTG | ATT | 1092 |
|---|---|---|---|---|---|---|---|---|---|---|---|---|---|---|---|---|
| Arg | Gln | Val | Ile | Leu | Lys | Cys | Ala | Ala | Glu | Ile | Asn | Leu | Pro | Val | Ile | |
| | | | 210 | | | | | 215 | | | | | 220 | | | |

| GAA | GAG | CCG | ATG | ACA | AAA | GGC | GAT | TTA | TTA | ACA | ATG | GAT | GAA | ATT | ATT | 1140 |
|---|---|---|---|---|---|---|---|---|---|---|---|---|---|---|---|---|
| Glu | Glu | Pro | Met | Thr | Lys | Gly | Asp | Leu | Leu | Thr | Met | Asp | Glu | Ile | Ile | |
| | | 225 | | | | | 230 | | | | | 235 | | | | |

| GTG | TCT | TCT | GTT | TCA | TCT | GAA | GTG | ACA | CCG | GTT | ATC | GAT | GTG | GAT | GGT | 1188 |
|---|---|---|---|---|---|---|---|---|---|---|---|---|---|---|---|---|
| Val | Ser | Ser | Val | Ser | Ser | Glu | Val | Thr | Pro | Val | Ile | Asp | Val | Asp | Gly | |
| 240 | | | | | 245 | | | | | 250 | | | | | | |

| CAG | CAA | ATT | GGT | GCA | GGT | GTT | CCT | GGT | GAA | TGG | ACT | CGT | AAA | TTG | CAA | 1236 |
|---|---|---|---|---|---|---|---|---|---|---|---|---|---|---|---|---|
| Gln | Gln | Ile | Gly | Ala | Gly | Val | Pro | Gly | Glu | Trp | Thr | Arg | Lys | Leu | Gln | |
| 255 | | | | | 260 | | | | | 265 | | | | | 270 | |

| AAA | GCA | TTT | GAG | GCA | AAA | TTA | CCA | ATT | TCA | ATT | AAT | GCC | | | TAATCTGTAT | 1285 |
|---|---|---|---|---|---|---|---|---|---|---|---|---|---|---|---|---|
| Lys | Ala | Phe | Glu | Ala | Lys | Leu | Pro | Ile | Ser | Ile | Asn | Ala | | | | |
| | | | | 275 | | | | | 280 | | | | | | | |

| AAATGATTAA | AAAGAGCTAC | CTAAAACTTG | GTTATTCGCC | AAGTTAGGAG | GGTAGCTCTT | 1345 |
|---|---|---|---|---|---|---|
| TTTTATAGAA | TAAAATATGC | ATGTATTCTC | CTGAAACGTC | ATGTAAAATA | AAAAAGATAG | 1405 |
| CGCCTTTAGT | CGATATCAC | | | | | 1424 |

( 2 ) INFORMATION FOR SEQ ID NO:3:

( i ) SEQUENCE CHARACTERISTICS:
        ( A ) LENGTH: 283 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met | Ala | Tyr | Ser | Leu | Trp | Asn | Asp | Gln | Ile | Val | Glu | Glu | Gly | Ser | Ile |
|---|---|---|---|---|---|---|---|---|---|---|---|---|---|---|---|
| 1 | | | | 5 | | | | | 10 | | | | | 15 | |

| Thr | Ile | Ser | Pro | Glu | Asp | Arg | Gly | Tyr | Gln | Phe | Gly | Asp | Gly | Ile | Tyr |
|---|---|---|---|---|---|---|---|---|---|---|---|---|---|---|---|
| | | | 20 | | | | | 25 | | | | | 30 | | |

| Glu | Val | Ile | Lys | Val | Tyr | Asn | Gly | His | Met | Phe | Thr | Ala | Gln | Glu | His |
|---|---|---|---|---|---|---|---|---|---|---|---|---|---|---|---|
| | | 35 | | | | | 40 | | | | | 45 | | | |

| Ile | Asp | Ala | Phe | Tyr | Ala | Ser | Ala | Glu | Lys | Ile | Arg | Leu | Val | Ile | Pro |
|---|---|---|---|---|---|---|---|---|---|---|---|---|---|---|---|
| | 50 | | | | | 55 | | | | | 60 | | | | |

| Tyr | Thr | Lys | Asp | Val | Leu | His | Lys | Leu | Leu | His | Asp | Leu | Ile | Glu | Lys |
|---|---|---|---|---|---|---|---|---|---|---|---|---|---|---|---|
| 65 | | | | | 70 | | | | | 75 | | | | | 80 |

Asn Asn Leu Asn Thr Gly His Val Tyr Phe Gln Ile Thr Arg Gly Thr
                85                  90                  95

Thr Ser Arg Asn His Ile Phe Pro Asp Ala Ser Val Pro Ala Val Leu
            100                 105                 110

Thr Gly Asn Val Lys Thr Gly Glu Arg Ser Ile Glu Asn Phe Glu Lys
            115                 120                 125

Gly Val Lys Ala Thr Leu Val Glu Asp Val Arg Trp Leu Arg Cys Asp
        130                 135                 140

Ile Lys Ser Leu Asn Leu Leu Gly Ala Val Leu Ala Lys Gln Glu Ala
145                     150                 155                 160

Ser Glu Lys Gly Cys Tyr Glu Ala Ile Leu His Arg Gly Asp Ile Ile
                165                 170                 175

Thr Glu Cys Ser Ser Ala Asn Val Tyr Gly Ile Lys Asp Gly Lys Leu
            180                 185                 190

Tyr Thr His Pro Ala Asn Asn Tyr Ile Leu Asn Gly Ile Thr Arg Gln
        195                 200                 205

Val Ile Leu Lys Cys Ala Ala Glu Ile Asn Leu Pro Val Ile Glu Glu
    210                 215                 220

Pro Met Thr Lys Gly Asp Leu Leu Thr Met Asp Glu Ile Ile Val Ser
225                 230                 235                 240

Ser Val Ser Ser Glu Val Thr Pro Val Ile Asp Val Asp Gly Gln Gln
            245                 250                 255

Ile Gly Ala Gly Val Pro Gly Glu Trp Thr Arg Lys Leu Gln Lys Ala
            260                 265                 270

Phe Glu Ala Lys Leu Pro Ile Ser Ile Asn Ala
        275                 280

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

Val Ile Phe Tyr Leu Ala Leu
1               5

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

Leu Pro Ile Ser Ile Asn Ala
1               5

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GCCATCTCCT TGCATGCACC ATTCC　　　　　　　　　　　　　　　　　　　　　　　　　25

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CCCTCGCAAG CTCGTCCGGA GGCAAATCGC TGAATATTCC　　　　　　　　　　　　　　40

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CGCAGATCTA CTATGGCATA CTCATTATGG　　　　　　　　　　　　　　　　　　　30

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CATGCCATGG ATCCTCCTTT TAGGTAGCTC TTTTTAATC　　　　　　　　　　　　　39

( 2 ) INFORMATION FOR SEQ ID NO:10:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGCGGATCCT CGTCATGAAC AGAACTGACG AACTCCG　　　　　　　　　　　　　　37

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

ACGCGTCGAC TCAGAAGCGG GTATCTACCG CAGAGG　　　　　　　　　　　　　　　36

( 2 ) INFORMATION FOR SEQ ID NO:12:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GGAAGATCTT ACATCATCAA CCAGATCGAT TCTG                    34
```

( 2 ) INFORMATION FOR SEQ ID NO:13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CGCGGATCCA TTATGGTTAC AGAAGGGAAG TCC                     33
```

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
CCGCTCGAGC CCGACGCACT TTGCGCCGA                          29
```

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
CCCAAGCTTA TCAGGCTCTG GGAGGCAG                           28
```

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
CGCGGATCCA CTATGACCCG TCCGATACAG GCC                     33
```

( 2 ) INFORMATION FOR SEQ ID NO:17:

( i ) SEQUENCE CHARACTERISTICS:

(A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TGCCATGCAT GCCTACAGTT GCTGACCAGC CGG    33

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CGCGGATCCA CTATGCAAGC GGCAACAGTC GTC    33

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGAGCATGCT TATTCAATAT ACTTCATCGC CAC    33

(2) INFORMATION FOR SEQ ID NO:20:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TTTAGCGCAT GCAAGGAGGA TCAACTATGA ACATTTCAAG GAGAAAG    47

(2) INFORMATION FOR SEQ ID NO:21:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

AGCTTTGTCG ACGGGCCCTT ACTTAAAACG ATCCAAAC    38

(2) INFORMATION FOR SEQ ID NO:22:

(i) SEQUENCE CHARACTERISTICS:
        (A) LENGTH: 42 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:22:

CGCGGATCCA CTATGACCAC GAAGAAAGCT GATTACATTT GG    42

( 2 ) INFORMATION FOR SEQ ID NO:23:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CAGCGTGCAT GCTTATTGAT TAACTTGATC TAACCAGC    38

( 2 ) INFORMATION FOR SEQ ID NO:24:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CCGGAATTCA CGTTGTGTCT CAAAATCTCT GAT    33

( 2 ) INFORMATION FOR SEQ ID NO:25:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CCGCTGCAGG CCGTCCCGTC AAGTCAGCGT AATG    34

( 2 ) INFORMATION FOR SEQ ID NO:26:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TTTGGATCCT CCTTAGTACA TGCAACC    27

( 2 ) INFORMATION FOR SEQ ID NO:27:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

TTTGAATTCG GATGAAGATT CTTGCTCGAT TGT    33

(2) INFORMATION FOR SEQ ID NO:28:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
GATCCTAGGT ACCGGTGCGG CCGCATGCTG ACTGACTGAA GATCCCGGGC GATTCTACGC    60
CCGGGTTTTT TATG                                                     74
```

(2) INFORMATION FOR SEQ ID NO:29:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
TCGACATAAA AAACCCGGGC GTAGAATCGC CCGGGATCTT CAGTCAGTCA GCATGCGGCC    60
GCACCGGTAC CTAG                                                     74
```

(2) INFORMATION FOR SEQ ID NO:30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
GACCTCGAGG CACTTTGCGC CGAATAAATA CCTGTG                             36
```

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

```
GACCTGCAGC ACCAGGCGTT TAAGGGCACC AATAAC                             36
```

(2) INFORMATION FOR SEQ ID NO:32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

```
TTTGGATCCA AGATGAACAT TCAAGGAGA AAG                                 33
```

( 2 ) INFORMATION FOR SEQ ID NO:33:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:33:

AGCTTTGTCG ACGCATGCTT ACTTCTTAAA ACGATCCAAA C    41

PREPARATION OF D-AMINO ACIDS BY DIRECT FERMENTATIVE MEANS

BACKGROUND OF THE INVENTION

1. Field of the Invention

The present invention relates to materials and methods for the production of D-amino acids. In particular, the present invention relates to the preparation of both natural and unnatural D-amino acids using recombinant host cells. Specifically, the invention relates to a fermentation process using recombinant cells to produce enantiomerically pure D-amino acids.

2. Background of the Invention

With the exceptions of glycine, threonine, and isoleucine, each of the common, naturally-occurring amino acids exist as one of two optical isomers, termed levorotatory or dextrorotatory, depending upon the direction in which they cause a plane of polarized light to rotate. Glycine, having no asymmetric carbon, has no optical isomers. Threonine and isoleucine, each having two asymmetric carbons, have four optical isomers each. Some amino acids, such as alanine and glutamine are dextrorotatory, producing a positive (right-handed) rotation. Others, such as phenylalanine and tryptophan, are levorotatory, producing a negative (left-handed) rotation. Thus, amino acids may be referred to as l- or d-amino acids in order to reflect their chirality in isolation. Specific rotation produced by a given amino acid varies with temperature and pH.

By convention, amino acids are also referred to as D or L (as opposed to the d or l designations referred to above) based upon whether the configuration about the α-carbon of the amino acid corresponds to the D or L stereoisomer (enantiomer) of glyceraldehyde, the arbitrary standard. Based upon that standard, most naturally-occurring amino acids are L-amino acids, despite the fact that some of them are dextrorotatory (d) when placed in aqueous solution at neutral pH. Most enzymes which act upon amino acids have asymmetric binding domains which recognize only the L-form of the amino acid. Accordingly, most naturally-occurring proteins comprise L-amino acids.

There are, however, exceptions wherein D-amino acids are produced and utilized by cells. Principal among these is the production of D-glutamate and D-alanine by certain microorganisms. D-glutamate and D-alanine are primarily produced in bacterial cells and are utilized in murein synthesis. In the absence of D-glutamate and D-alanine, a defective bacterial cell wall is produced, resulting in cell lysis. Most bacteria produce D-amino acids not by direct synthesis, but through conversion of the corresponding L-amino acid by an amino acid-specific racemase. For example, many bacterial cells possess an alanine racemase which catalyzes bidirectional conversion between L-alanine and D-alanine, resulting in a racemic (50:50) mixture of L- and D-alanine. Similarly, a glutamate racemase produces a racemic mixture of D-glutamate and L-glutamate, the former for incorporation into the cell wall and the latter for, inter alia, formation of protein. The specificity of those two enzymes is demonstrated by the fact that the lack of either one results in cell lysis due to defective cell wall formation.

Certain bacteria, such as members of the genus Bacillus, possess an alternative to racemases for making D-amino acids in the form of an enzyme known as D-aminotransferase. Such an enzyme reversibly catalyzes the transamination of various D-amino acids and corresponding α-keto acids. In PCT Publication WO 91/05870, Manning reports a method for microbial synthesis of D-alanine and D-glutamate via catalysis by an aminotransferase. While Manning reports, at page 2, the use of a *Bacillus sphaericus* D-aminotransferase, that publication actually only reports the cloning, isolation, and use of a thermophilic species of D-aminotransferase which is not capable of effectively catalyzing synthesis of more than trace amounts of the D-amino acid. Moreover, Manning fails to report any means for isolating or using a *Bacillus sphaericus* D-aminotransferase or any other D-aminotransferase which catalyzes the synthesis of enantiomerically pure D-amino acids.

Evidence that Manning's reference to a *Bacillus sphaericus* D-aminotransferase is an error is found at page 2 of the Manning publication, wherein Manning states that the D-aminotransferase DNA was cloned onto plasmid pICT113. As reported in Stoddard, et al., *J. Mol. Biol.*, 196: 441–442 (1987), plasmid pICT113 carries the thermophilic species of D-aminotransferase and not the *Bacillus sphaericus* species. The significance of that fact is that the thermophilic species cannot effectively catalyze significant production of a D-phenylalanine and, therefore, is useless in recombinant methods for production of a D-phenylalanine acid.

Prior to the present application, the only report of a *Bacillus sphaericus* D-aminotransferase is a partial C-terminal sequence found in *Transaminases*, Christen, et al., (eds.), 464 (1985). However, as will be apparent from the present invention that partial sequence is wrong and is not useful in isolating the *Bacillus sphaericus* D-aminotransferase. Accordingly, no prior reference reports a *Bacillus sphaericus* D-aminotransferase in the production, by recombinant means or otherwise, of a D-amino acid. Other D-aminotransferases have been isolated but, unlike that produced by the *Bacillus sphaericus* species, D-phenylalanine is a relatively poor substrate for those enzymes. Tanizawa et al., *J. Biol. Chem.*, 264: 2445–2449 (1989).

This invention provides recombinant materials and methods for producing enantiomerically-pure natural and unnatural D-amino acids.

SUMMARY OF THE INVENTION

The present invention relates to materials and methods for production of natural and unnatural D-amino acids. In particular, the present invention relates to a fermentation method for the production of D-amino acids using recombinant host cells.

Specifically, the invention relates to a method for producing a D-amino acid in a cell, comprising:

(a) incorporating into the cell a D-aminotransferase gene and a L-aminodeaminase gene;

(b) culturing the cell in a cell culture medium; and (c) isolating the D-amino acid from the cell culture medium.

The invention also relates to a method for producing D-phenylalanine in a cell, comprising:

(a) incorporating into the cell a D-aminotransferase gene, a L-aminodeaminase gene and means for increasing production of phenylpyruvate;

(b) culturing the cell in a cell culture medium; and (c) isolating the D-phenylalanine from the cell culture medium.

The methods of the present invention may further comprise the step of introducing a D-aminodeaminase gene mutation into the cell such that the D-aminodeaminase gene is nonfunctional.

The invention also relates to the preparation of recombinant cells for use in the production of enantiomerically pure D-amino acids.

DETAILED DESCRIPTION OF THE INVENTION

Figure 1:
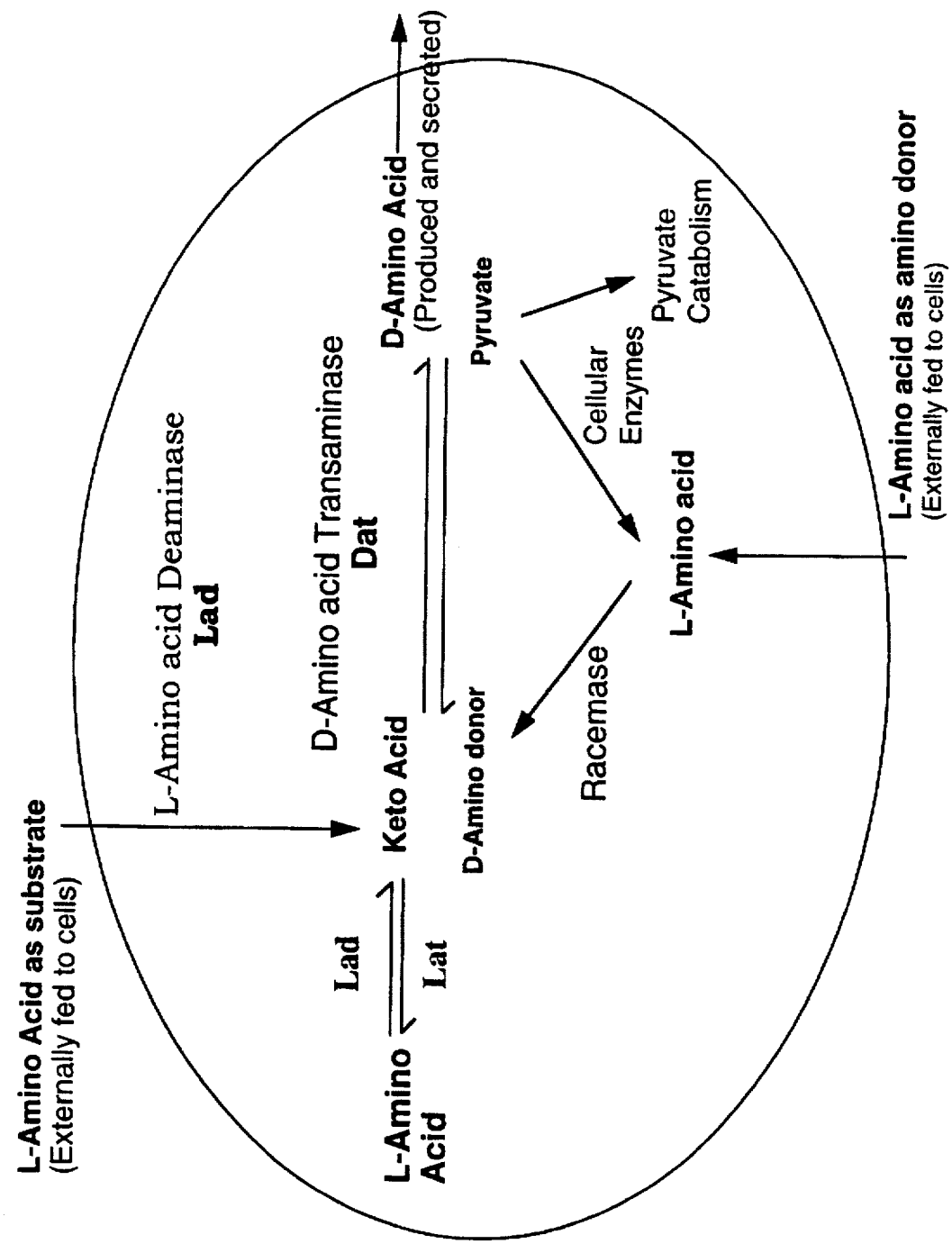
FIG. 1. is a general scheme illustrating the method of the present invention for the production of D-amino acids.

The present invention relates to materials and methods for the production of D-amino acids. The general method of the present invention is illustrated in FIG. 1. The invention relates to a method in which a D-aminotransferase gene (dat) and a L-aminodeaminase gene (lad) are introduced into a bacterial cell. The D-aminotransferase gene product, i.e., the D-aminotransferase enzyme (Dat), catalyzes a transamination reaction between a D-amino acid substrate and a keto acid precursor. In the transamination reaction the keto acid precursor is converted to its corresponding D-amino acid and the D-amino acid substrate is converted to its keto acid form. Thus, the D-amino acid substrate serves the function of being an amino donor in the transamination reaction.

A L-aminotransferase gene product, i.e., a L-aminotransferase enzyme (Lat) is naturally present in cells. The D-aminotransferase gene product competes in the cell with the L-aminotransferases gene product for the keto acid precursor as a substrate. The L-aminotransferase enzyme catalyzes the transamination reaction between an L-amino acid substrate and the keto acid precursor to form the L-amino acid of the form of the keto acid precursor. However, if a L-aminodeaminase gene is introduced into the cell, its gene product catalyzes the deamination of any L-amino acid present in the cell to its corresponding keto acid form. The keto acid formed due to deamination of the L-amino acid provides further keto acid precursor for use as a substrate by the D-aminotransferase enzyme. Conversion of the keto acid precursor to its corresponding D-amino acid form by D-aminotransferase is irreversible as there is no D-aminodeaminase gene present in the cell to produce a D-aminodeaminase enzyme to deaminate the D-amino acid product.

In one preferred embodiment of the present invention, genes encoding enzymes for the production of amino acid substrates and keto acid precursors may also be incorporated into the cell in order to overproduce the desired substrates that are available to the D-aminotransferase and L-aminotransferase enzymes. The genes incorporated may be racemase genes or genes that encode rate limiting enzymes involved in the biosynthesis of amino acid substrates or keto acid precursors. Alternatively, the amino acid substrates and/or the keto acid precursors may be provided as part of the culture medium for the cells during the production of the D-amino acids. In the case of the cell culture medium containing L-amino acids or racemic amino acids as the substrate, a racemase gene is preferably incorporated into the cell in order to provide an overproduction of a racemase enzyme to convert the L-amino acid added as part of the cell culture medium to D-amino acid. In addition, the presence of the L-aminodeaminase gene product will deaminate the L-amino acid present in the cell to produce its corresponding keto-acid precursor for use as a substrate by D-aminotransferase enzyme.

Cells which are suitable for use in the method of the present invention include, but are not limited to the following bacterial cells, such as *Bacillus subtilis, Bacillus sphaericus, Bacillus stearothermophilus,* Pseudomonas, Klebsiella, Salmonella, Brevibacterium, Micrococcus, Corynebacterium and *Escherichia coli*. In another preferred embodiment of the method of the present invention the cell is *Escherichia coli*.

In another preferred embodiment of the present invention, the use of *Bacillus stearothermophilus* cells have the additional advantage of being moderate thermophiles thereby allowing the preparation of D-amino acids to be performed at elevated temperatures where reaction rates are faster. Accordingly, production times for the preparation of D-amino acids may be reduced.

In one preferred embodiment an L-aminodeaminase gene from *Proteus myxofaciens* and a D-aminotransferase gene from *Bacillus sphaericus* are introduced into a cell. Both of these genes encode enzymes that have very broad substrate ranges as shown in the following Table 1. The substrates include both natural and unnatural D- and L-amino acids. In addition, the substrate range for these enzymes may be increased by mutation of the respective genes using standard mutation procedures.

TABLE 1

Natural and unnatural amino acid substrates for Lad and Dat enzymes.

| Lad Substrate | Dat Substrate |
| --- | --- |
| Alanine | Pyruvic Acid |
| Phenylalanine | Phenylpyruvic acid |
| Isoleucine | alpha-ketoisocaproate |
| Leucine | alpha-ketoisovaleric acid |
| Tryptophan | Indole-3-Pyruvic acid |
| Tyrosine | Hydroxy phenylpyruvic acid |
| Valine | alpha-ketoisovaleric acid |
| Arginine | 5-Guanidino-2-Oxovaleric Acid |
| Asparagine | 2-Oxosuccinamic Acid |
| Glutamine | Not tested |
| Methionine | 2-Oxo-4-(methylthio)butyric acid |

TABLE 1-continued

Natural and unnatural amino acid substrates for Lad and Dat enzymes.

| Lad Substrate | Dat Substrate |
| --- | --- |
| Ornithine | 5-Amino-2-Oxopentanoic acid |
| Serine | 3-hydroxypyruvic acid |
| Norleucine | 2-Oxohexanoic acid |
| Norvaline | 2-Oxopentanoic acid |
| Dihydroxyphenyl alanine | Dihydroxyphenylpyruvic acid |
| Citrulline | alpha-Oxo-gamma-ureidonovaleric acid |
| Cysteine | Not tested |
| Histidine | 2-Oxo-4-Imidazolepropionic acid |
| Lysine | 6-Amino-2-Oxohexanoic acid |

In another preferred embodiment an L-aminodeaminase gene from *Proteus mirabilis* and a D-aminotransferase gene from *Bacillus sphaericus* are introduced into a cell.

In one preferred embodiment of the present invention, the preferred host cell is an *Escherichia coli* strain pIF3. The *Escherichia coli* strain pIF3 is derived from a RY347 strain which may be obtained from the American Type Culture Collection, 12301 Parklawn Drive, Rockville, Md. 20852, U.S.A. (ATCC Accession Number 69766). The pIF3 strain differs from RY347 in that wild copies of the L-aminotransaminase genes typB+ and ilvE have been introduced to the chromosome cell by transduction with a bacteriophage P1 as described in Miller et al., *A Short Course in Bacterial Genetics*, Cold Spring Harbor Laboratory Press (1992), incorporated by reference herein. The tyrB+ and ilvE genes encode L-aminotransaminase enzymes that convert keto acid precursors to their corresponding L-amino acid form.

The reintroduction of the wild type aminotransaminase genes tyrB+ and ilvE into pIF3 cells has the added benefit of improving cell growth over that of RY347, presumably due to some undefined additional function of the L-aminotransaminase gene products. In particular, preferred L-aminotransaminase genes, include but are not limited to aspC, tyrB and ilvE.

The chromosomes of the cells used in the production of D-amino acids of the present invention may be mutated using standard techniques, as described in Miller et al., *A Short Course in Bacterial Genetics*, Cold Spring Harbor Laboratory Press (1992), incorporated by reference herein. In one particular embodiment, a dadA gene mutation is introduced into the *Escherichia coli* cells such that the dadA gene is nonfunctional. *Escherichia coli* cells have a dad operon which comprises the genes dadA and dadX. The dadX gene encodes alanine racemase enzyme which is involved in racemizing amino acids between its D- and L-forms. The dadA gene encodes a D-aminodeaminase which carries out the oxidative deamination of a range of D-amino acids. The dad operon is induced in the presence of D-alanine and produces the D-aminodeaminase and D-alanine racemase enzymes. The DadX and DadA enzymes form a membrane complex which is involved in the uptake and catabolism of D-alanine to pyruvate. The DadA enzyme can also deaminate other D-amino acids such as D-phenylalanine. Accordingly, in *Escherichia coli* cells that are involved in the overproduction of D-amino acids, it is advantageous to mutate the dadA gene in order to prevent production of the DadA enzyme.

Additionally, *Escherichia coli* strains bearing mutations in L-aminotransaminase genes aspC, ilvE, tyrB or in the D-aminodeaminase dadA gene may be obtained from the coli Genetic Stock Center (Yale University, New Haven, Conn.). For example, the following *Escherichia coli* strains, DG30, DG31, DG34, and DG, having mutations in L-aminotransaminase genes aspC, ilvE, and tyrB and the *Escherichia coli* strain, EB105 having a mutation in the D-aminodeaminase dadA gene may be obtained the coli Genetic Stock Center.

Mutations including deletions may be introduced to the chromosome of the cell in a site directed fashion using temperature sensitive recombinant plasmids, which carry in vitro generated fragments of the target gene into the host cell chromosome. For example, plasmid pHSG415 disclosed in U.S. Pat. No. 5,354,672 in which the temperature sensitive nature of the plasmid replication control region can be used to identify recombinant events between the plasmid and the host cell chromosome. The deleted copy of a target gene on the plasmid may be exchanged for the wild type copy of the same gene on the cell chromosome using pHSG415. Subsequent loss of the plasmid from the host cell renders the cell mutated in the target gene. Accordingly, pHSG415 provides an effective means in which to either mutate a host cell chromosome or to reintroduce a wild type gene back into a host cell chromosome that had been mutated.

In one preferred embodiment of the present invention, a method for producing D-phenylalanine in a cell comprises, incorporating into the cell a D-aminotransferase gene and a L-aminodeaminase gene. The D-aminotransferase gene product catalyzes a transamination reaction between a D-alanine substrate and a keto acid precursor, phenylpyruvate, to produce D-phenylalanine and pyruvate. The substrates D-alanine and phenylpyruvate are normally present in the cell, the former for incorporation into the cell wall, the latter as the last precursor in the pathway leading to L-phenylalanine biosynthesis. In addition, the naturally present L-aminotransferase gene product catalyzes the transamination reaction between L-alanine and phenylpyruvate to produce L-phenylalanine and pyruvate. However, introduction of the L-aminodeaminase gene into the cell results in production of L-aminodeaminase enzyme which deaminates most of the L-phenylalanine synthesized back to phenylpyruvate while the rest of the L-phenylalanine present is used in the production of protein. The phenylpyruvate produced as a result of the deamination reaction can be utilized by the D-aminotransferase enzyme as a substrate to produce more D-phenylalanine. Production of D-phenylalanine in the cell is irreversible because there is no D-aminodeaminase gene product present in the cell to deaminate the D-phenylalanine.

In the production of D-amino acids using the method of the present invention it is desirable to have increased levels of D-amino acid substrate for use as an amino donor in the transamination reaction. For example, in the preparation of D-phenylalanine addition of D-alanine to the cell assures sufficiently high levels of D-alanine substrate for the transamination reaction.

In a preferred embodiment of the present invention a racemic mixture of alanine is added to the cells as part of the cell culture medium during fermentation. Additionally, a cyctoplasmic alanine racemase gene (alr) encoding an alanine racemase enzyme is introduced into the cell. The alanine racemase enzyme maintains the 50/50 D-, L-alanine equilibrium in the cell. As the amount of D-alanine in the cell is being consumed due to the action of the D-aminotransaminase enzyme, the alanine racemase enzyme converts L-alanine to D-alanine. In this manner, all of the D-, L-alanine mixture is made available to the D-aminotransferase enzyme as D-alanine substrate for use as an amino donor in the transamination reaction, other than the small amount incorporated into the cell wall. In one preferred embodiment, the alr gene incorporated into the cell is cloned from *Salmonella typhimurium*.

Other suitable amino donors that may be added to cell cultures during the production of D-amino acids include L-alanine, L-glutamate, L-phenylalanine, L-aspartate or a racemic mixture one of the aforementioned L-amino acids. Preferably, a racemase gene is also incorporated into the cell, such as glutamate racemase, aspartate racemase or phenylalanine racemase depending on the amino donor present. Accordingly, D-aminotransaminase enzyme has increased amounts of D-amino donor substrate available for use in the transamination reaction.

In order to increase the production of D-phenylalanine in the cell, the amount of the keto acid precursor, i.e., phenylpyruvate, may be increased in the cell by introducing genes that encode the rate limiting enzymes that produce phenylpyruvate. Phenylpyruvate production from the cellular aromatic amino acid biosynthetic pathway is regulated by two rate limiting enzymes, PheA and AroH. Introduction of the genes that encode PheA and AroH into the cell results in an overproduction of phenylpyruvate. Accordingly, increasing the amount of phenylpyruvate provides more substrate for the D-aminotransferase gene product to convert to D-phenylpyruvate.

The amount of the keto acid precursor in the cell may also be increased by addition of the corresponding L-amino acid to the cell. In the case of the addition, of a L-amino acid, the L-aminodeaminase enzyme deaminates the L-amino acid to form the corresponding keto acid precursor. The keto acid precursor can then be used as a substrate by the D-aminotransferase enzyme to be converted to its corresponding D-amino acid.

The present invention also relates to a recombinant cell, comprising an exogenous D-aminotransferase gene and an exogenous L-aminodeaminase gene. The recombinant cell of the present invention may further comprise a D-aminodeaminase gene mutation in the cell such that the D-aminodeaminase gene is nonfunctional. The recombinant cell of the present invention may further comprise an exogenous alanine racemase gene, an exogenous aroH gene and an exogenous pheA gene. The exogenous D-aminotransferase gene may be a *Bacillus sphaericus* D-aminotransferase gene, the exogenous L-aminodeaminase gene may be a *Proteus myxofaciens* L-aminodeaminase gene or a *Proteus mirabilis* L-aminodeaminase gene and the exogenous racemase gene may be a *Salmonella typhimurium* racemase gene.

Figure 2:
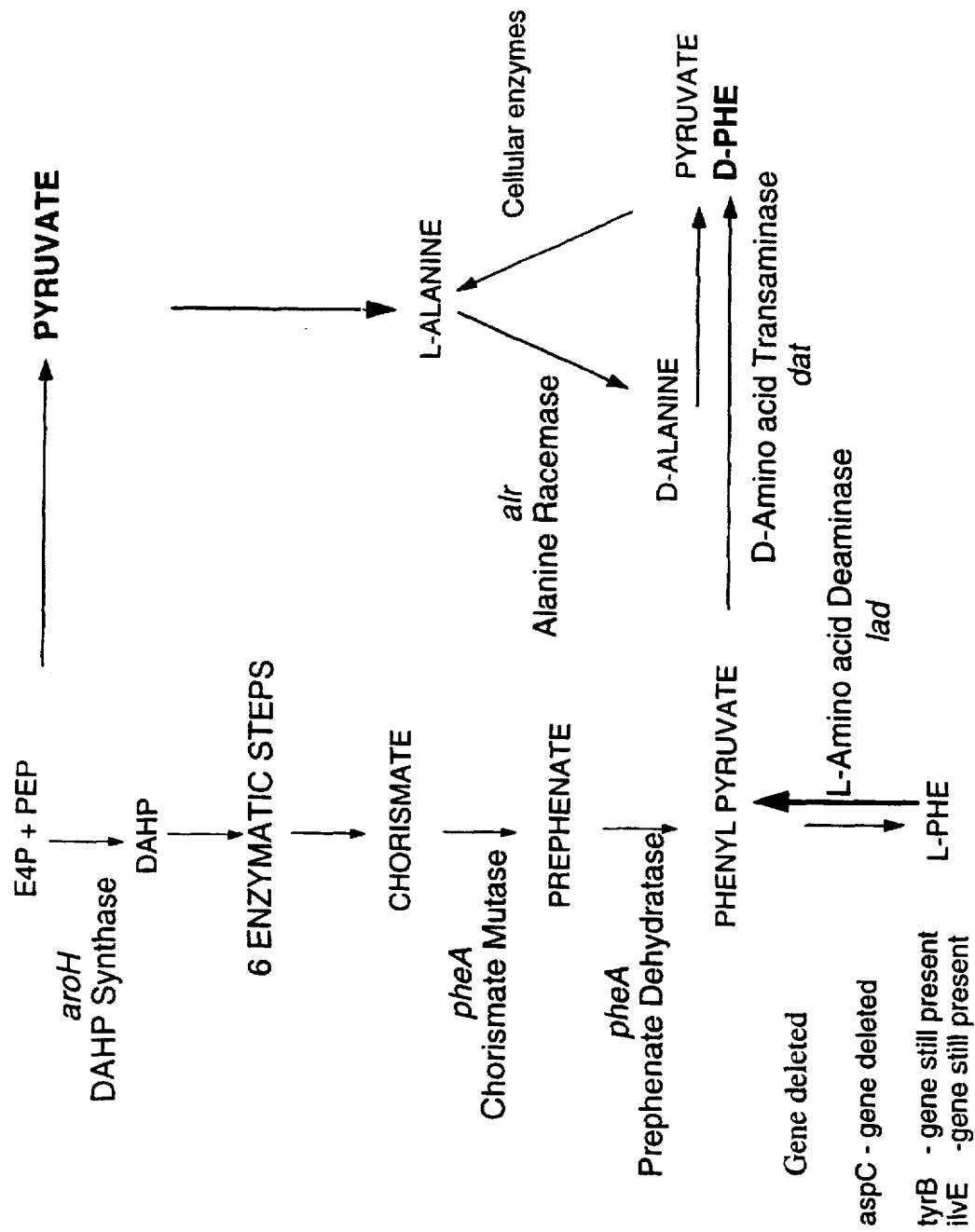
FIG. 2. is a scheme illustrating the production of D-phenylalanine using the method of the present invention. The following abbreviations are used in FIG. 2. E4P is erythrose-4-phosphate, PEP is phosphoenolpyruvate, and DAHP is 3-deoxy-D-arabinoheptulosonate-7-phosphate.

Cultures of recombinant cells of the present invention are used to produce enantiomerically pure D-amino acids. The percentage enantiomeric excess (ee) of a D-amino acid over an L-amino acid produced using the disclosed method may be determined by subtracting the amount of L-amino acid present from that of the D-amino acid present, dividing by the total amount of D-, and L- amino acid and multiplying by 100. In a preferred embodiment, D-phenylalanine is produced in substantially pure form and in high yields. The method of production of D-phenylalanine is illustrated in FIG. 2.

Using cultures of recombinant cells of the present invention with the addition of D-, L-alanine and L-phenylalanine as additional sources of D-alanine and phenylpyruvate substrates for the D-aminotransferase gene product resulted in the production of 13.66 g/l of D-phenylalanine and 0.47 g/l of L-phenylalanine, a 94% enantiomeric excess. In the case where only D-, L-alanine was added to the cultures during the fermentation process resulted in the production of 4.15 g/l of D-phenylalanine and no L-phenylalanine, a 100% enantiomeric excess. In contrast, when no D-, L-alanine or L-phenylalanine was added to the cell cultures during the fermentation process, 1.12 g/l of D-phenylalanine and 0.47 g/l of L-phenylalanine is produced, a 41% enantiomeric excess.

The D-amino acids produced according to the method of the present invention may be isolated using procedures well-known to those skilled in the art. For example, one method of isolating the D-amino acids prepared using the disclosed method is as follows. On completion of fermentation, the fermentation broth is decanted from the cells. The broth may be reduced in volume to increase the concentration of the D-amino acid product. The reduction of the broth is typically carried out by heating the broth to temperatures of between 30° C. to 100° C. under a vacuum. The D-amino acid is then precipitated by adjusting the pH of the broth to a range of ±1° C. from the isoelectric point of the amino acid product. During the pH adjustment the D-amino acid product will precipitate. Following, precipitation the D-amino acid is separated from the broth by standard methods, which may include filtration, centrifugation or decanting. The isolated D-amino acid product is then washed and dried.

In *Escherichia coli*, the amino acids alanine, aspartic acid, glutamic acid, phenylalanine, tyrosine, valine, leucine and isoleucine are synthesized directly from their keto acid precursors. In addition to adding either L-amino acids or racemic mixtures to the recombinant cells during fermentation, the keto acid precursor of a desired amino acid may be overproduced by the introduction of genes that produce the rate limiting enzymes for a particular keto acid.

The following examples are provided to more specifically set forth and detail particular embodiments of practicing the present invention. They are for illustrative purposes only and it is recognized that minor changes and alterations can be made to the starting materials and/or the process parameters. To the extent that any such changes do not materially alter the process or final end product they are deemed as falling within the spirit and scope of the present invention as recited by the claims that follow.

Example 1

ISOLATION OF D-AMINOTRANSFERASE DNA

Cultures of *Bacillus sphaericus*, were obtained from the American Type Culture Collection, ATCC, (ATCC Accession No. 10208), as a source of D-aminotransferase DNA. Cultures were streaked on unsupplemented LB medium and allowed to grow overnight at 37° C. In order to prepare chromosomal DNA, a single colony was used to inoculate 50 ml Luria Broth in a 1 L flask which was shaken overnight at 300 rpm and 37° C. Cells were then harvested by centrifugation at 10,000 G for 5 minutes, washed in 0.85% saline and centrifuged again at 10,000 G for 5 minutes. The resulting pellet was re-suspended in 5 ml of 10 mM glucose, 25 mM Tris HCl, pH 8.0, and 10 mM ethylenediamine tetraacetic acid (EDTA). An aliquot of 50 µl RNase A was added and the solution was mixed gently. Subsequently, 10 ml of 0.4% sodium dodecyl sulphate (SDS) and 100 µg/ml protease K were added to the mixed solution which was then incubated at 37° C. until clear. Sodium acetate, pH 5.2, was then added to a final concentration of 300 mM. Gentle phenol extractions were carried out using a volume of phenol approximately equal to the aqueous phase until no white precipitate was visible at the phase interface. The aqueous phase was then removed and the chromosomal DNA was precipitated using 2.5 volumes of ethanol. The DNA pellet was removed and re-solubilized in 300 mM sodium acetate, pH 5.2. Ethanol precipitation was carried out and the DNA pellet was removed, dried and dissolved in 2 ml distilled water. The DNA concentration was determined to be 150 µg/ml. In addition to the procedure described above, standard procedures are known for the isolation of bacterial DNA and are reported, for example, in *Current Protocols in Molecular Biology*, 2.4.1–2.4.5 (Ausubel, et al., eds., 1994), incorporated by reference herein.

The chromosomal DNA obtained as described above was then partially digested with MboI. Ideal digestion, yielding fragments in the range of 2–10 kb, was obtained using 13 µg chromosomal DNA and digesting for 40 minutes with 2.5 MboI (New England Biolabs, Beverly, Mass.). Approximately 13 µg chromosomal DNA prepared as indicated above was partially digested with 2.5 U of MboI in a total volume of 100 µl at 37° C. in Biolabs MboI buffer. Samples of 17 µl were taken at 5, 10, 20, 30, 40 minutes and a sample of 15 µl was taken at 50 minutes. All samples were heated to 65° C. in order to destroy any restriction enzyme present in the sample which was then placed on ice. A 5 µl aliquot of each sample was electrophoresed on a 0.8% agarose gel using TBE buffer as described in Sambrook, et al. (eds.), *Molecular Cloning: A Laboratory Manual* (Cold Spring Harbor Laboratory Press): 6.3–6.32 (1989), incorporated by reference herein. From the electrophoresis data, it was determined that the sample taken at 40 minutes contained the majority of the DNA in the 2–10 kb size range and it was those fragments which were used to construct a library in plasmid pIF306 for expression of the D-aminotransferase.

Plasmid pIF306 was derived from pBR322 (New England Biolabs, Beverly, Mass.). In order to construct pIF306, a modified pheA promoter was inserted between unique HindIII and SphI sites on pBR322. Within the HindIII to SphI insert there exists unique BamHI and BglII sites. The modified pheA promoter was derived from that characterized in co-owned U.S. Pat. No. 5,120,837 to Fotheringham et al. which is incorporated by reference herein, such that the sequence was as follows:

then treated with a PCR purification kit (Qiagen) in order to isolate the DNA fragment free of enzyme.

The pIF306 vector fragment was ligated to the fragments from the 40 minute partial digest see above) of ATCC 10208 chromosomal DNA by combining approximately 20 ng of vector fragment with the remaining approximately 12 µl of the 40 minute partial digest. Ligation was accomplished using a Takara Ligation Kit (Takara Biochemicals, PanVera Corporation, Madison, Wis.) according to the manufacturer's instructions. The ligation was carried out at 17° C. for 2 hours, at which time the DNA was recovered using a PCR purification kit (Qiagen) in a final volume of 50 µl. The resulting plasmids were introduced into *Escherichia coli*, XL1-Blue (Stratagene, La Jolla, Calif.) by electroporation using a Bio-Rad Gene Pulser™ set to 2.5 kv with 25 µF capacitance and a Bio-Rad pulse controller set to 200 ohms resistance.

Transformants were plated on LB medium supplemented with 50 µg/ml ampicillin. Approximately 20,000 transformants were produced and pooled. Plasmid DNA was then isolated as reported in *Molecular Cloning: A Laboratory Manual* (Sambrook, et al., eds. 2d ed. 1989), incorporated by reference herein. The resulting plasmid DNA was incorporated into *Escherichia coli*, strain WM335 by electroporation using a BioRad Gene Pulser™ set to 2.5 kv with 25 µF capacitance and a Bio-Rad pulse controller set to 200 ohms resistance. Strain WM335 may be obtained from the Phabagen Collection, Department of Molecular Cell Biology, State University of Utrecht, The Netherlands and was reported in Lugtenberg, et al., *J. Bacteriol.*, 114: 499–506 (1973), incorporated by reference herein. Cells were pulsed in BioRad Gene Pulser™ cuvettes with a 0.2 cm gap. *Escherichia coli* cells to be transformed were grown (50 ml cultures) to an optical density of 0.7 at 600 nm. The cells were then recovered by centrifugation at 10,000 G for 5 minutes and washed in 30 ml deionized distilled water. The cells were re-spun and re-suspended in 200 µl deionized distilled water and 40 µl of cells were combined with 10 µl of the recovered ligation mix and placed in an electroporation cuvette. A single pulse was applied to the cuvette and 500 µl SOC medium (GIBCO/BRL, Gaithersburg, Md.) was added and mixed with the cell suspension. The contents of the cuvette were then transferred to a 20 ml pvc tube and

```
HindIII              -35                              -10
AAGCTTTTTTGTTGACAGCGTGAAAACAGTACGGGTATAATACT BamHI      Start
AAAGTCACAAGGAGGATCCACTATGACATCGGAAAACCCGTTACT HaeII
GGCGCT  (SEQ ID NO: 1).
```

Vector DNA was prepared by digesting pIF306 to completion with BamHI and BglII, each of which produces ends compatible with those produced by MboI. The digest was carried out at 37° C. in a total volume of 20 µl for 2 hours using 0.5 µg of plasmid DNA and 2 units of each enzyme. Fragments of 4.25 kb and 1.25 kb were produced and separated by electrophoresis on a 1% agarose TBE gel. The desired 4.25 kb fragment was excised from the gel and recovered using a Gel Extraction Kit (Qiagen Inc., Chatsworth, Calif.). That fragment was then treated with calf intestinal phosphatase (New England Biolabs, Beverly, Mass.) at 37° C. for 1 hour in a volume of 20 µl with 1 unit of enzyme in Biolabs buffer #2 according to the manufacturer's instructions in order to dephosphorylate the ends of the DNA and to prevent re-circularization. The mixture was incubated for 30 minutes at 37° C. Cells were then plated on appropriate media and selected as described below. Numerous medium for transforming/transfecting DNA into microorganisms are known and may be used in methods according to the invention. See, e.g., Chang, et al. (eds.), *Guide to Electroporation and Electrofusion* (Academic Press, 1992).

Figure 3:
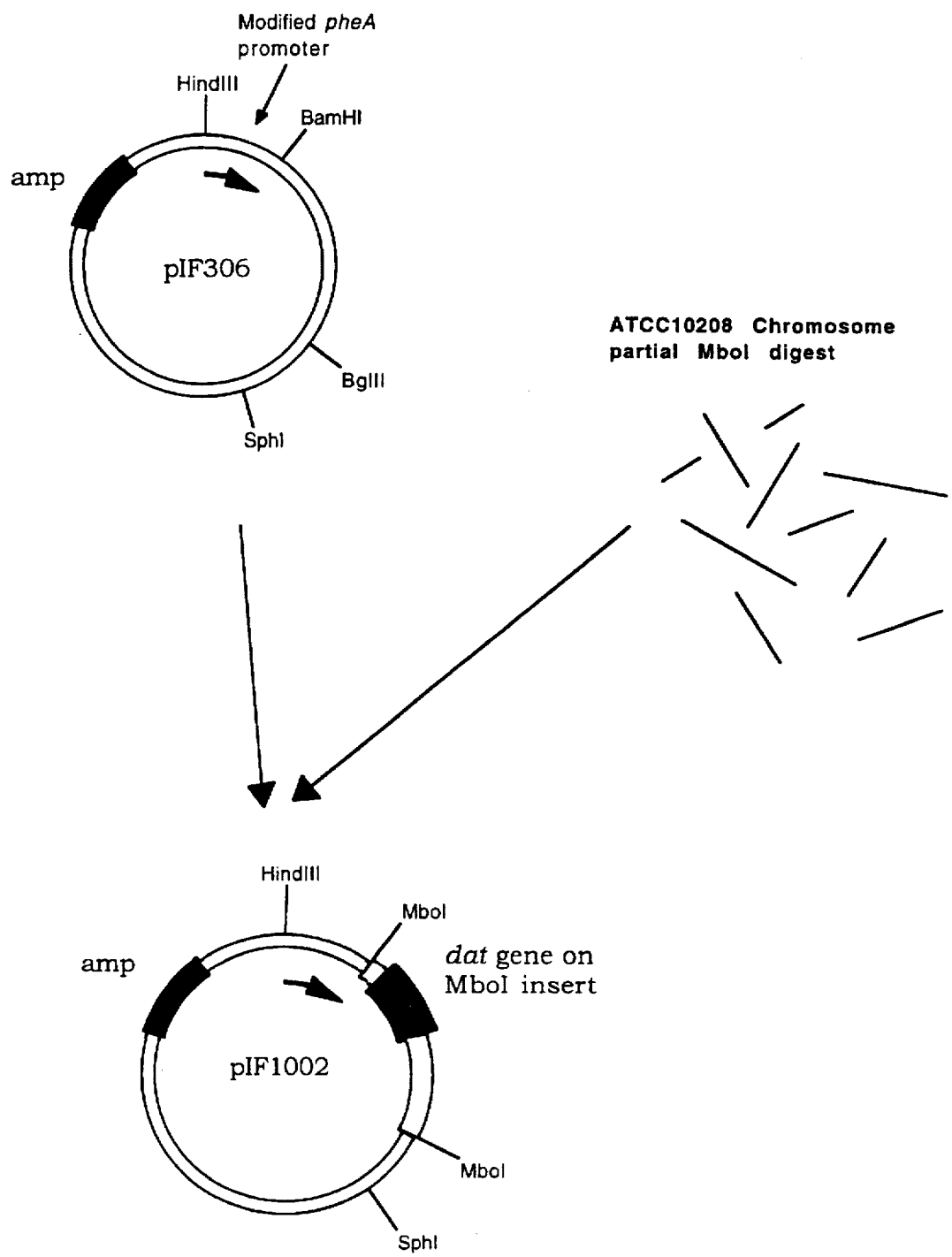
FIG. 3. is a schematic diagram showing construction of plasmid pIF1002.
Figure 4:
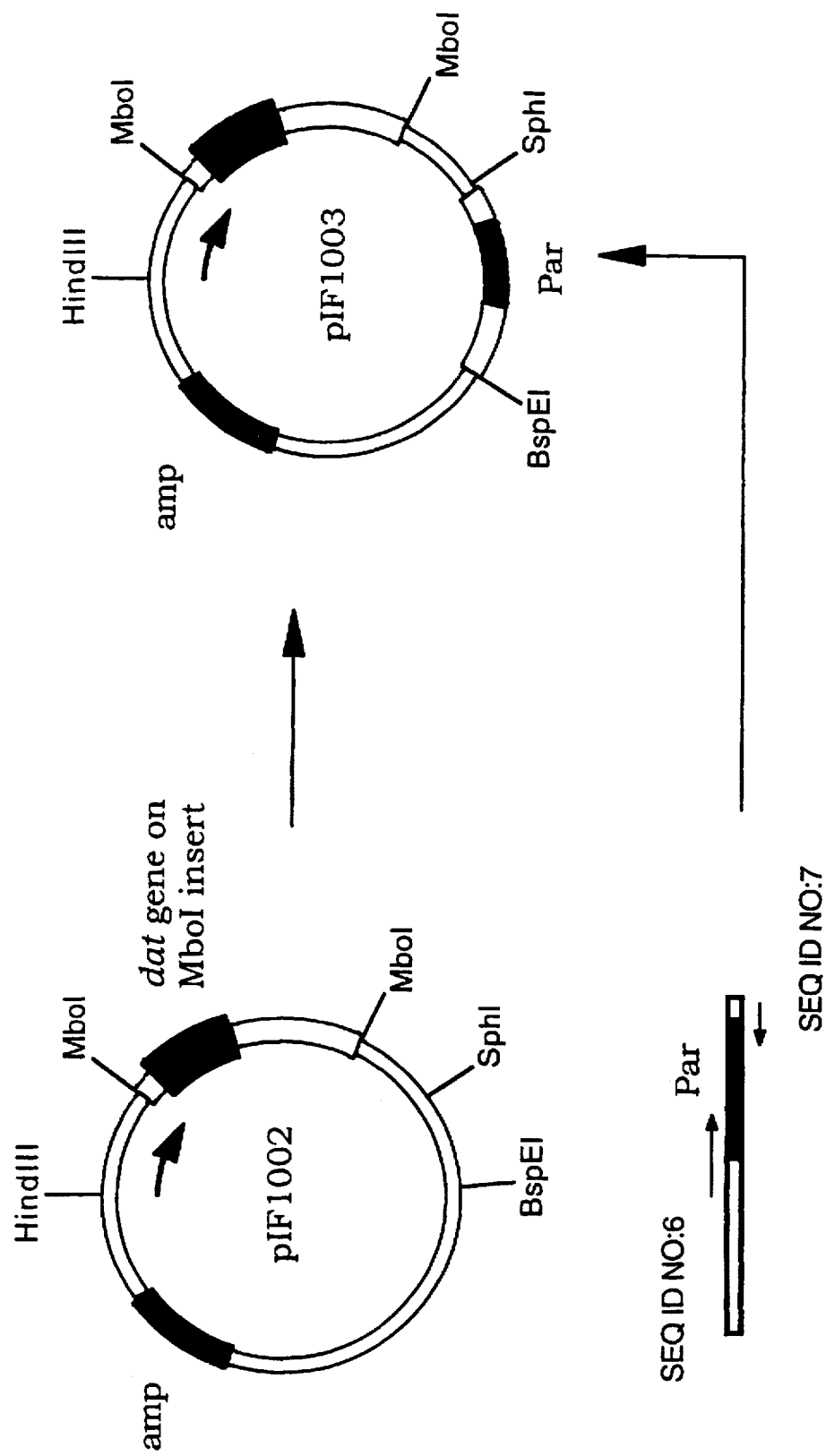
FIG. 4. is a schematic diagram showing construction of plasmid pIF1003.
Figure 5:
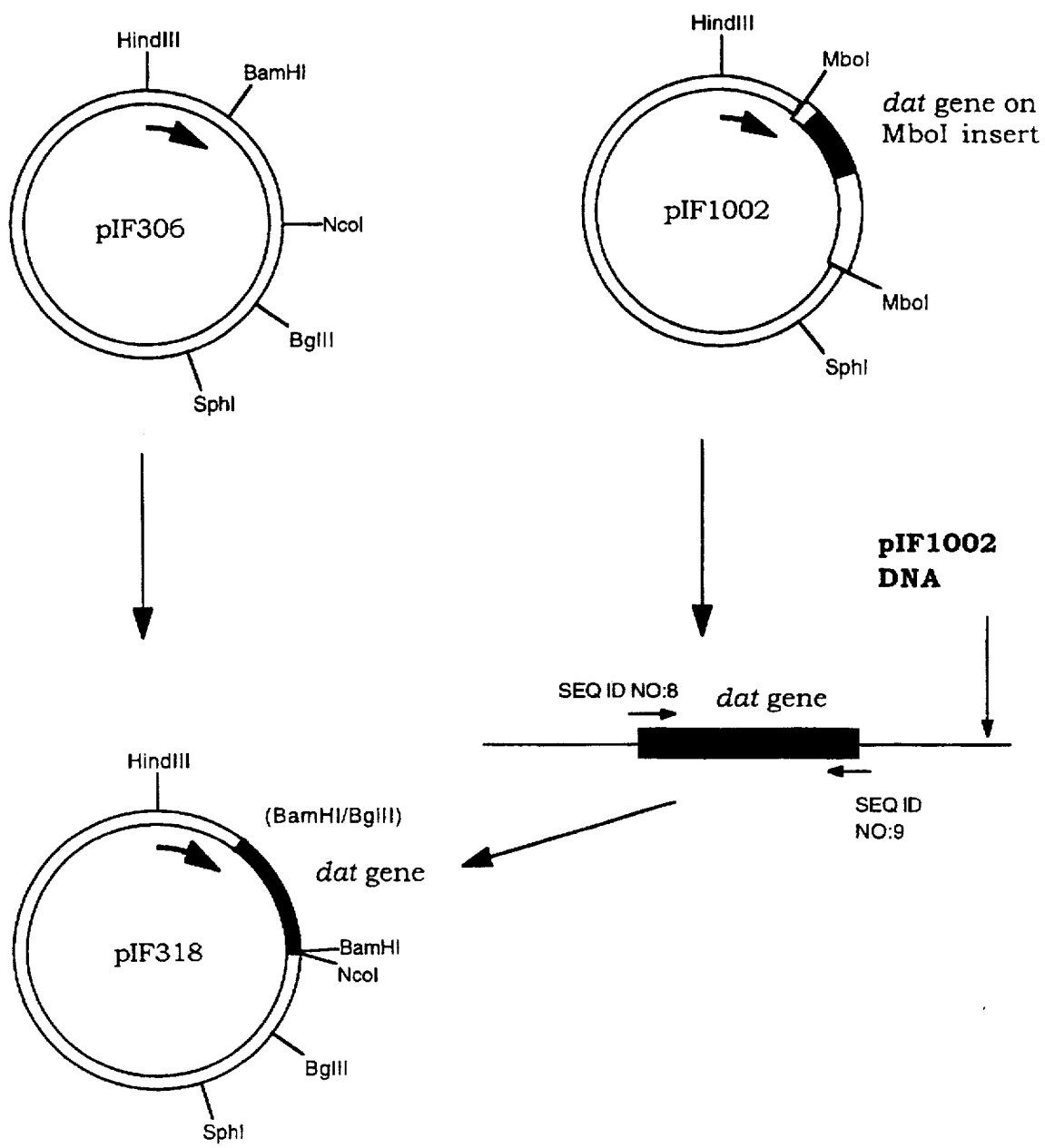
FIG. 5. is a schematic diagram showing construction of plasmid pIF318.

Transformants were plated on LB medium supplemented with 50 µg/ml thymine and 60 µg/ml ampicillin but lacking D-glutamate. Only those transformants able to make D-glutamate survive on that medium. According to reports in the literature, all such cells should have necessarily been transformants carrying the dat gene of *Bacillus sphaericus* because *Bacillus sphaericus* was thought to lack a glutamate racemase. However, two different classes of transformants were isolated by the procedure described above, one carrying the dat gene and the other carrying a glutamate racemase. The racemase-containing clone was designated pIF1001 and the dat-containing clone was designated pIF1002. FIG. 3 is a schematic diagram showing construction of pIF1002.

Figure 6:
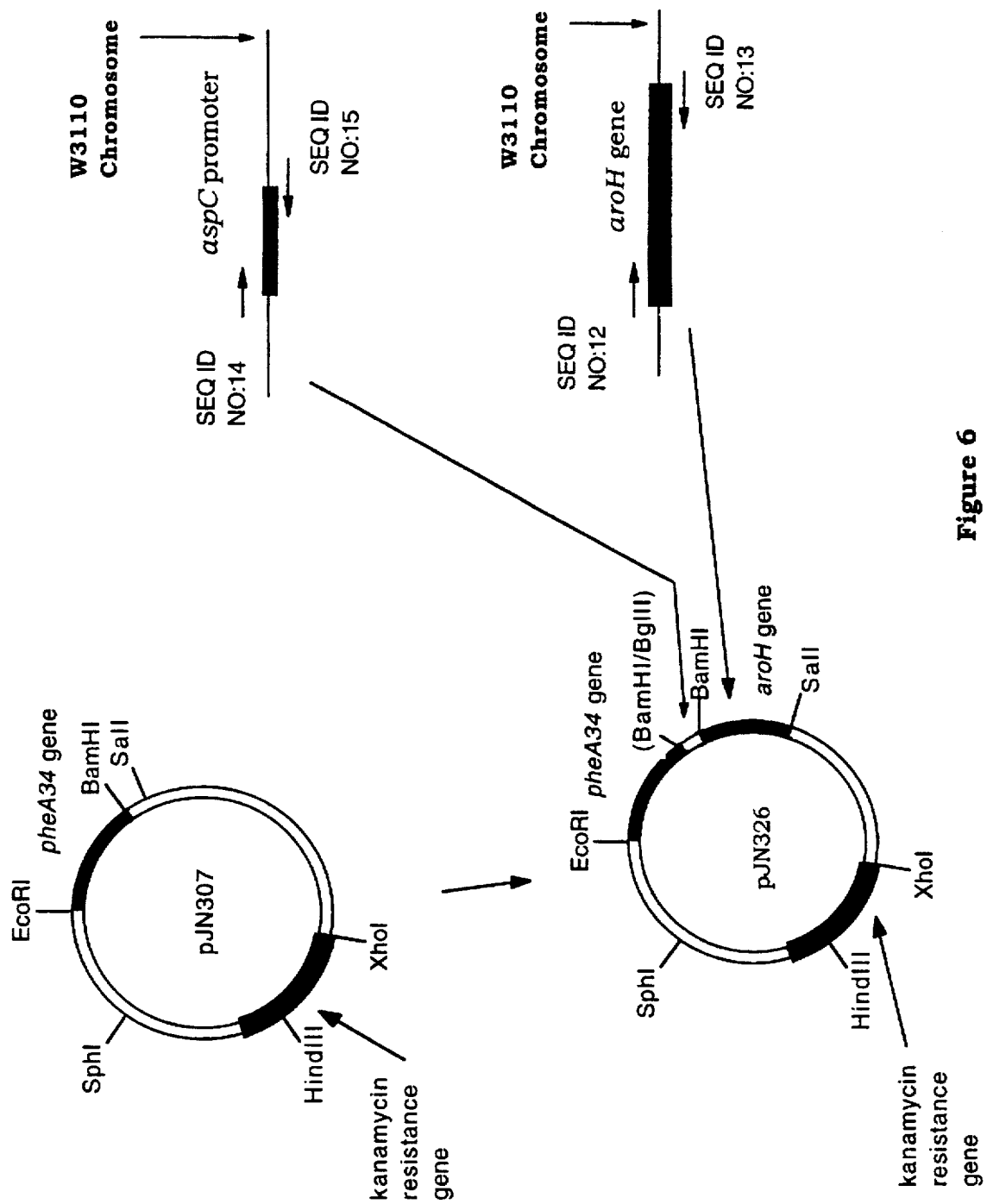
FIG. 6. is a schematic diagram showing construction of plasmid pJN326.

In each case, the clones were mapped by restriction endonuclease digestion and the genes were sequenced. The sequence of the dat gene and the deduced amino acid sequence of the encoded protein are shown in SEQ ID NOS: 2 and 3. It was found that the dat gene had a high degree of sequence homology with the only other known dat gene sequence. See Tanizawa, et al., *J. Biol. Chem.*, 264: 2450–2454 (1989). However, the C-terminal amino acid sequence of the D-aminotransferase encoded by the *Bacillus sphaericus* dat gene in pIF1002 did not agree with that of the only other published report of a *Bacillus sphaericus* D-aminotransferase in which only a C-terminal sequence was published. That sequence, reported in Transaminases, Christen, et al. (eds.), 464 (1995) was Val-Ile-(Phe-Tyr)-Leu-Ala-Leu (SEQ ID NO: 4). In contrast, the correct C-terminal sequence as provided in the present invention is Leu-Pro-Ile-Ser-Ile-Asn-Ala (SEQ ID NO: 5). It was attempted, without success, to use the sequence reported in Christen in order to isolate a *Bacillus sphaericus* D-aminotransferase-encoding gene.

Both clones were then subjected to a biological assay for the presence of the dat gene. That assay was reported in *Methods in Enzymology*, 113: 108–113 (19), incorporated by reference herein. Briefly, cultures of pIF1001 or pIF1002 in WM335 cells were set up in 50 ml of LB medium supplemented with 50 μg/ml thymine and 200 μg/ml ampicillin. The cultures were grown overnight in 500 ml flasks in a shaking incubator at 37° C. Cells were harvested by centrifugation at 10,000 G for 5 minutes and washed in 50 mM potassium phosphate at pH 8.5. The cells were re-spun and taken up in 1 ml 50 mM potassium phosphate at pH 8.5. The cells were then lysed using a French Pressure Cell at 1000 lbs/in$^2$ and the lysates were centrifuged at 14,000 G in a microfuge for 30 minutes, at which time supernatant was extracted by micropipette. The resulting cell extracts were assayed using the lactatedehydrogenase-coupled assay as reported in *Methods in Enzymology*, 113: 108–113 (19), incorporated by reference herein. The assay mixture contained 0.3M potassium phosphate, pH 8.5, 25 mM D-alanine, 25 mM α-keto-glutarate, 0.1 mM NADH, 70 μg/ml lactate dehydrogenase and 50 μl cell extract. The reaction was started by addition of the NADH and lactate dehydrogenase to the other components in a 1 ml cuvette at 25° C. The reaction produced a change in absorbance at 338 nm as evidence of oxidation of NADH. To correct for non-specific oxidation, control assays were run using an assay mixture lacking cell extract.

As an additional control, assays were run using an assay mixture lacking D-alanine. Extracts of untransformed WM335 cells and controls produced essentially identical changes in absorbance; whereas WM335 cells bearing pIF1002 showed changes in absorbance in excess of 30-fold greater than controls. The dat-containing clone had levels of activity about 100-fold greater than extracts of *Bacillus sphaericus*, a consequence of overexpression on the high copy number plasmid, pIF306. Plasmid pIF1001 had activity identical to that of the controls.

Example 2

CONSTRUCTION OF PLASMID pIF1003

Plasmid pIF1003 was a derivative of pIF1002 which carries the partition (Par) locus of plasmid pLG338 (Stoker et al., Gene 18: 355–341 (1982)). The partition locus of plasmid pLG338 (Stoker et al., Gene 18: 355–341 (1982). The partition locus controls plasmid partitioning during cell division and in doing so confers increased segregational stability on plasmid vectors. It is useful in reducing or eliminating the need for antibiotic selection in plasmid maintenance. The partition locus can be isolated from pLG338 using PCR with the oligonucleotide primers:

5'GCCATCTCCTTGCATGCACCATTCC 3' (SEQ ID NO: 6)

5'CCCTCGCAAGCTCGTCCGGAG-GCAAATCGCTGAATATTCC 3' (SEQ ID NO: 7)

The resulting 992bp fragment was then digested with the restriction enzymes SphI and BspEI (New England Biolabs, Beverly, Mass.) and the resulting 965 bp, SphI to BspEI fragment was isolated using a QIAquick gel extraction kit (QIAGEN) following electrophoresis on a 1% agarose TBE gel. This fragment was then ligated to the 5.8 kB DNA fragment produced by BspEI cleavage and partial SphI cleavage of pIF1002 to generate pIF1003. FIG. 4 is a schematic diagram showing construction of pIF1003.

Example 3

CONSTRUCTION OF PLASMID pIF321

In order to construct a vector which enables production of D-phenylalanine in a host cell, the dat gene was isolated from pIF1002 using PCR. Amplification of the dat-encoding region was accomplished using an Amplitaq™ PCR Kit (Perkin-Elmer, Norwalk, Conn.) in a 0.2 ml MicroAmp™ reaction tube (Perkin-Elmer, Norwalk, Conn.) to which was added 100 ng pIF1002 DNA (1 μl); 5 μl each of primers, MB1809 5' CGCAGATCTACTATGGCATACTCAT-TATGG 3' (SEQ ID NO: 8 ); and

MB1810 5' CATGCCATGGATCCTCCTTTTAGG-TAGCTCTTTTTAATC 3' (SEQ ID NO: 9)

at a concentration of 10 nanomoles/ml each; 2 μl each of dATP, dCTP, dTTP, and dGTP (10 mM each); 10 μl buffer comprising 15 mM $MgCl_2$, 500 mM $KCl_2$, 100 mM Tris (pH 8.3), and 0.01% gelatin; a Taq DNA polymerase (0.5 μl at 5 u/μl, Amplitaq™); and distilled water to a total volume of 100 μl. The tube was capped and placed in a Perkin Elmer 9600 Thermal Cycler. Amplification was carried out by pre-heating at 94° C. for 3 minutes, followed by 25 cycles of denaturation at 94° C. for 30 seconds, annealing at 50° C. for 30 seconds, and extension at 72° C. for 90 seconds. The reaction mixture was stored at 4° C.

The resulting approximately 914 bp PCR product was digested with BglII and NcoI and the product was then ligated into the 4.5 kb BamHI to NcoI fragment of pIF306 using a Ligation Kit (Takara Biochemicals) according to the manufacturer's instructions. The resulting plasmid was designated pIF318. Construction of pIF318 is shown in FIG. 5.

The pIF319 plasmid was based upon the pLG338 plasmid disclosed in co-owned U.S. Pat. No. 5,354,672, incorporated by reference herein, with the kanamycin resistance marker replaced by a chloramphenicol resistance marker to avoid conflict with a potential host strain, *Escherichia coli* HW857, which carries a kanamycin resistance gene. Plasmid pIF319 contains the pheA34 gene, as disclosed in co-owned U.S. Pat. No. 5,120,837, incorporated by reference herein, and the aroH gene in a synthetic operon between unique EcoRI and SalI sites in pLG338. The pheA34 allele contains a modification in the pheA coding sequence which substantially reduces phenylalanine-mediated feedback inhibition of the enzyme. It also contains a deregulated version of the pheA promoter region which lacks the attenuator sequence and allows increased expression of associated genes. The presence of pheA34 and aroH effectively deregulate pathways to phenylpyruvate in *Escherichia coli* W3110 and in any *Escherichia coli*, K12 strain. Plasmid pIF319 may also be derived from pJN307, disclosed in U.S. Pat. No. 5,120,837, by introduction of the *Escherichia coli* aroH gene between unique BamHI and SalI sites in pJN307 followed by introduction of the *Escherichia coli* aspC promoter into the BamHI site. The aroH gene was isolated from the *Escherichia coli* W3110 by PCR using primers 5'CGCGGATCCTCGTCATGAACAGAACT-GACGAACTCCG 3' (SEQ ID NO: 10) and 5' ACGCGTC-GACTCAGAAGCGGGTATCTACCGCAGAGG 3' (SEQ ID NO: 11). The resulting PCR fragment was cleaved with BamHI and SalI and ligated to the 8 kb fragment generated by similar cleavage of pJN307. The aspC promoter region was then inserted at the unique BamHI site in the resulting intermediate plasmid. The aspC promoter region was isolated from *Escherichia coli* W3110 by PCR using primers 5' GGAAGATCTTACATCATCAACCAGATCGATTCTG 3' (SEQ ID NO: 12) and 5' CGCGGATCCATTATGGTTACA-GAAGGGAAGTCC 3' (SEQ ID NO: 13). The resulting approximately 278 bp fragment was then cleaved with BglII and BamHI and ligated to the vector cleaved at a unique BamHI site. The resulting ligation results in a DNA sequence that cannot be cleaved with BglII and only singly with BamHI and, therefore, provides a simple means for verification of the orientation of the aspC promoter. The resulting construction is pJN326. Construction of pJN326 is shown in FIG. 6. Plasmid pJN319 was generated from pJN326 by deletion of most (520 bp) of the kanamycin resistance gene by cleavage with HindIII and XhoI and insertion of a DNA fragment encoding the chloramphenicol resistance gene of pHSG415. The chloramphenicol resistance gene of pHSG415 was isolated by PCR using the primers 5'CCGCTCGAGCCCGACGCACTTTGCGCCGA 3' (SEQ ID NO: 14) and

5' CCCAAGCTTATCAGGCTCTGGGAGGCAG 3' (SEQ ID NO:15).

Figure 7:
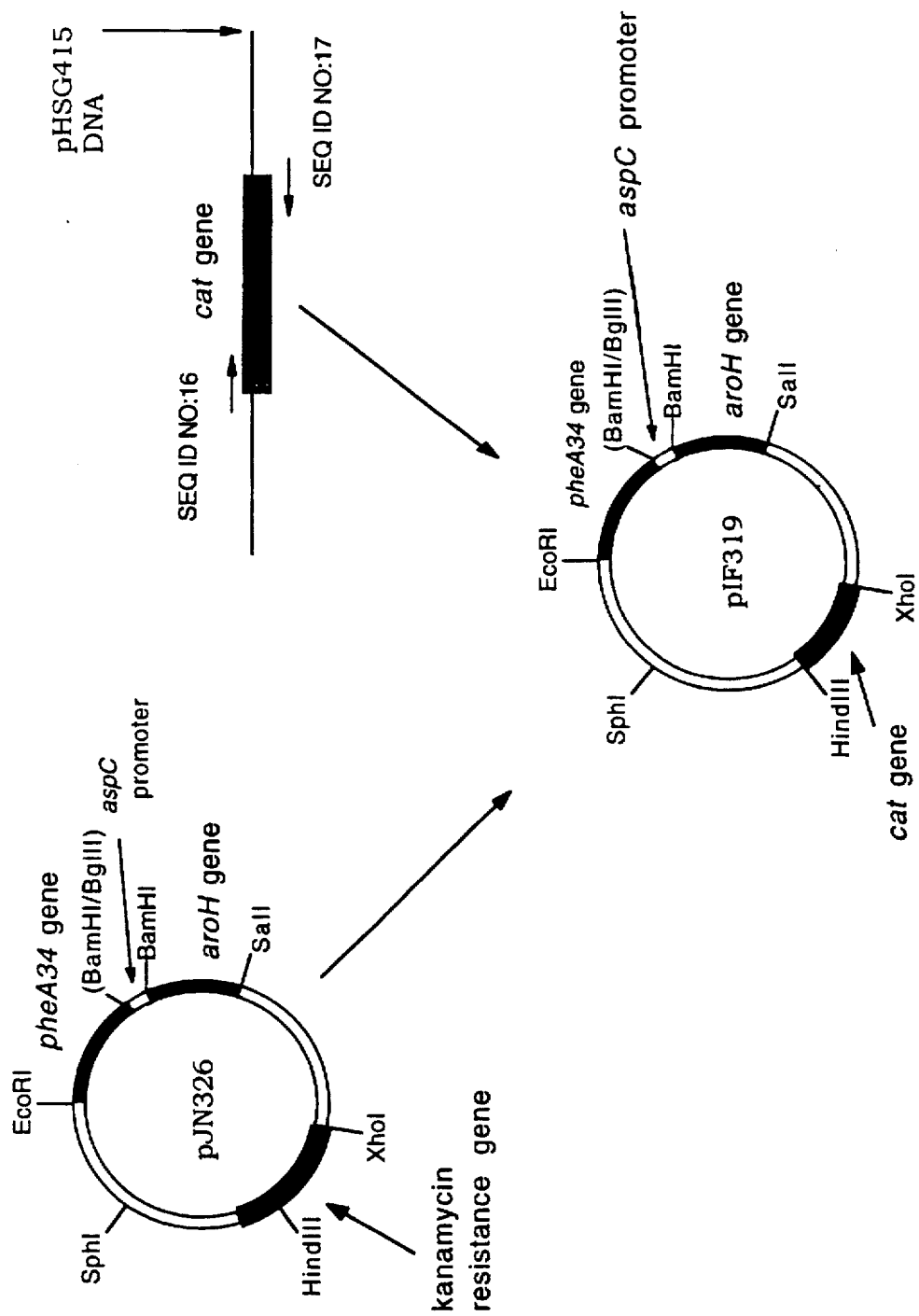
FIG. 7. is a schematic diagram showing construction of plasmid pIF319.

The resulting approximately 1191 bp fragment was cleaved with HindIII and XhoI and ligated to the 8.87 kb fragment generated by similar cleavage of pJN326. The resulting plasmid is pIF319. Construction of pJN319 is shown in FIG. 7.

The pIF318 plasmid was cleaved with BamHI and SphI for the insertion of a dadX gene in order to construct the pIF320 plasmid. The MB1810 primer referred to above contains a BamHI site (GGATCC) which overlaps the NcoI site in that primer. It is the BamHI site (and the downstream SphI site) that was used for introduction of dadX to form a synthetic operon comprising dat and dadX. The dadX gene sequence was obtained from the Genbank database, reference code ECODADAX. From that sequence, PCR primers MB1811, 5'CGCGGATCCACTATGACCCGTCCGATA-CAGGCC 3' (SEQ ID NO: 16) and

Figure 8:
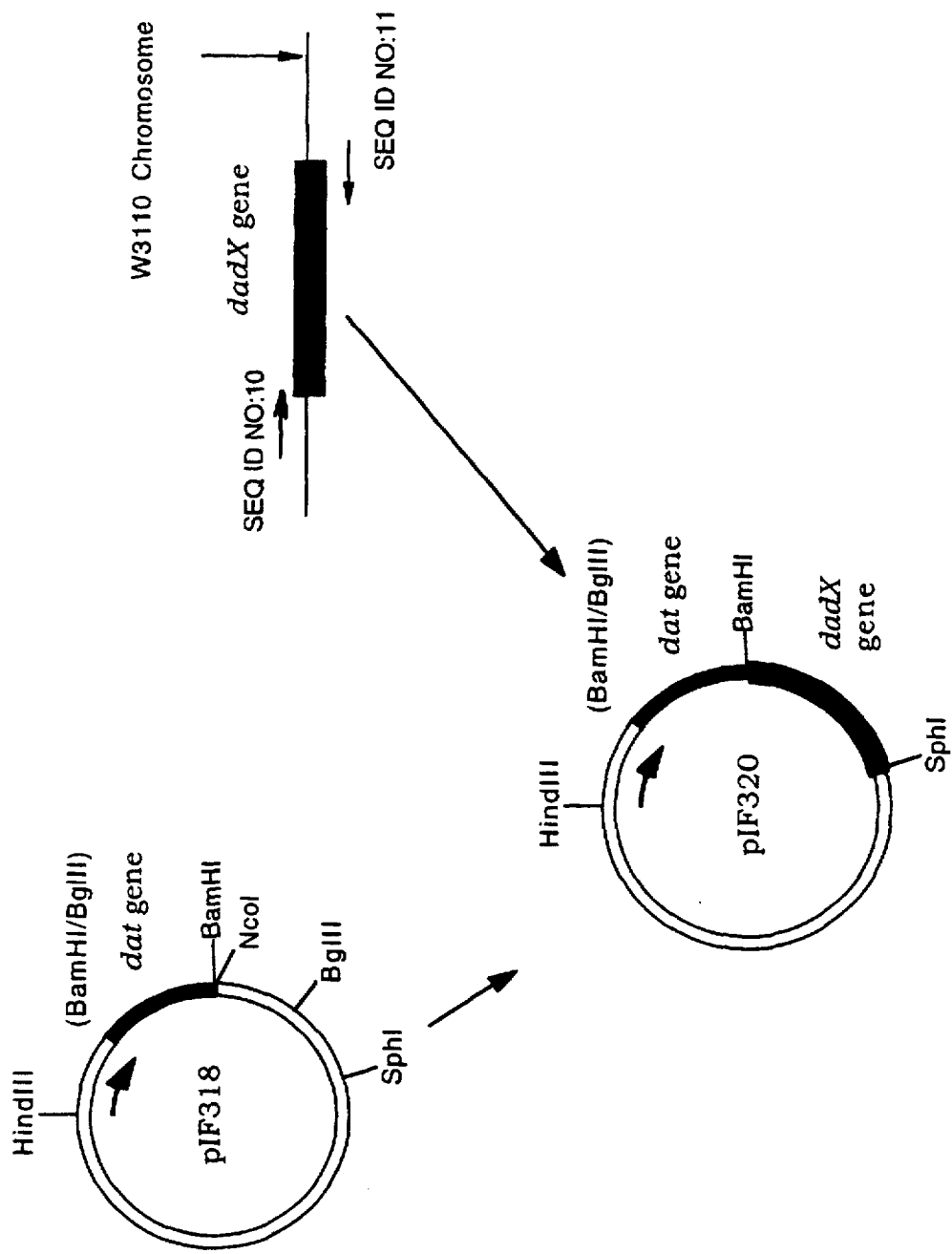
FIG. 8. is a schematic diagram showing construction of plasmid pIF320.

MB1816, 5' TGCCATGCATGCCTACAGTTGCTGAC-CAGCCGG 3' (SEQ ID NO: 17)

were designed and used to isolate the dadX gene from *Escherichia coli*, strain W3110 (ATCC Accession Number 27325). Amplification conditions were exactly as described above. The gene was isolated without its native promoter and ligated immediately downstream of the dat gene insert. Amplification results in an approximately 1171 bp fragment which was cleaved with BamHI and SphI and ligated to pIF318 which was similarly digested to form an approximately 4.8 kb fragment. The resulting plasmid was designated pIF320 and carries the dat and dadX genes in a synthetic operon. Construction of pIF320 is shown in FIG. 8.

Figure 9:
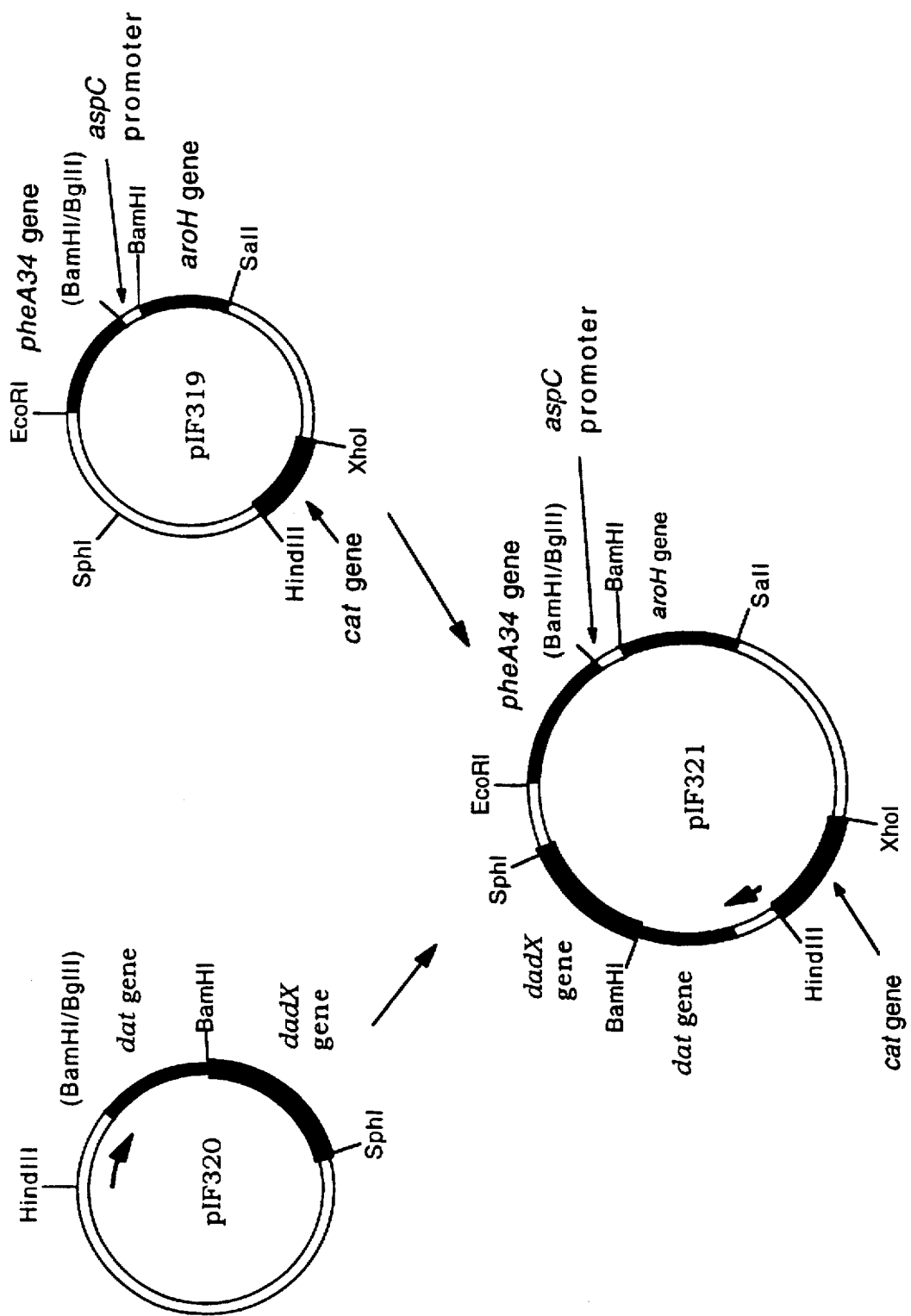
FIG. 9. is a schematic diagram showing construction of plasmid pIF321.

An additional plasmid, designated pIF321 was then constructed. Plasmid pIF321 was generated by cleaving pIF320 with HindIII and SphI and isolating the 2.1 kb fragment carrying the dat and dadX genes which was then ligated to the 9.2 kb fragment produced by similar cleavage of pIF319. Construction of pIF321 is shown in FIG. 9. The pIF321 plasmid contained dat and dadX genes of pIF320 isolated on a HindIII-to-SphI fragment (HindIII-promoter-dat-dadX-SphI) and ligated into pIF319, which contains the above-described pheA34 allele along with the aroH gene which encodes the tryptophan-dependent DAHP synthase of *Escherichia coli*.

Example 4

CONSTRUCTION Of PLASMID pIF333

Figure 10:
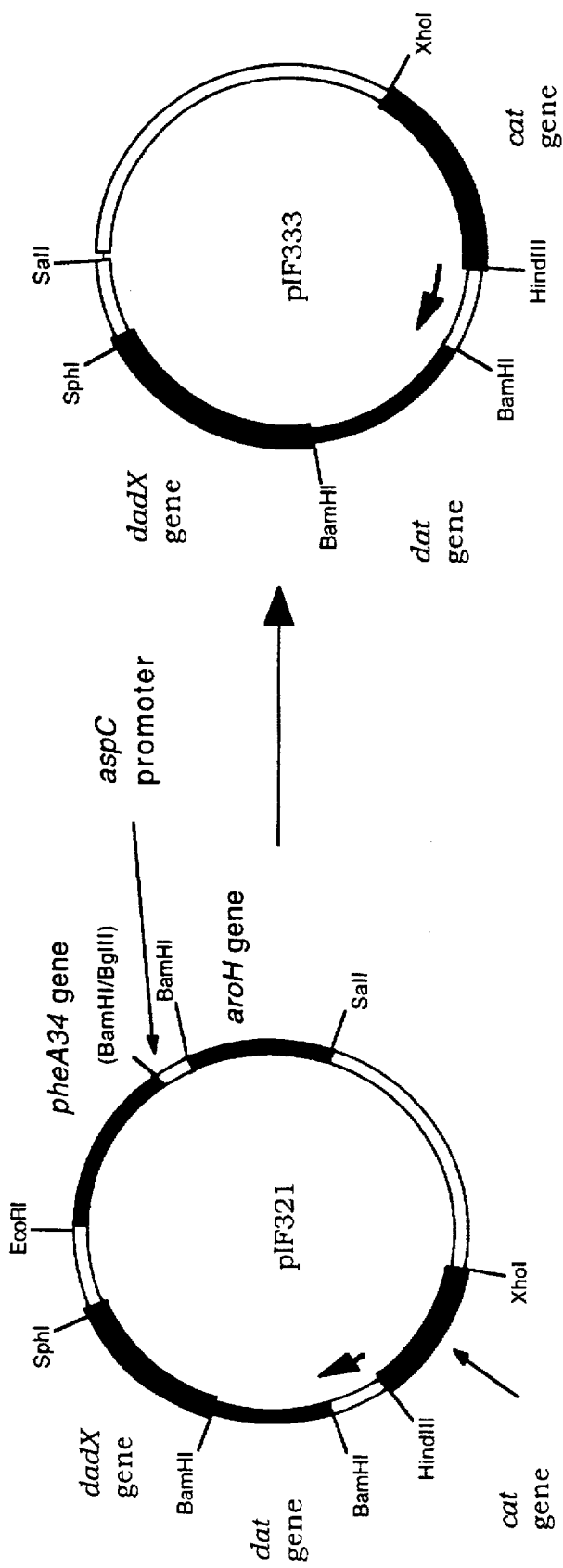
FIG. 10. is a schematic diagram showing construction of plasmid pIF333.

In order to generate plasmid pIF333, plasmid pIF321 was first cleaved using the enzymes SphI and SalI to yield fragments of 6.9 kB and 4.5 kB. The 6.9 kB fragment can be isolated using a QIAquick gel extraction kit (QIAGEN) following electrophoresis on a 1% agarose TBE gel. This fragment was then ligated to the 89 bp fragment generated from SphI and SalI cleavage of pBR322 (New England Biolabs, Beverly, Mass.) and similarly isolated from a 2% agarose TBE gel. The resulting plasmid is pIF333. Construction of pIF333 is shown in FIG. 10.

Example 5

CONSTRUCTION OF pALR18

The alr gene encoding alanine racemase was isolated from *Salmonella typhimurium* strain ATCC Accession Number 19585 obtained from the ATCC. The alr gene was isolated by PCR using the oligonucleotide primers:

5' CGCGGATCCACTATGCAAGCGGCAA-CAGTCGTC 3' (SEQ ID NO: 18)

5' GGAGCATGCTTATTCAATATACTTCATCGCCAC 3' (SEQ ID NO: 19)

Figure 11:
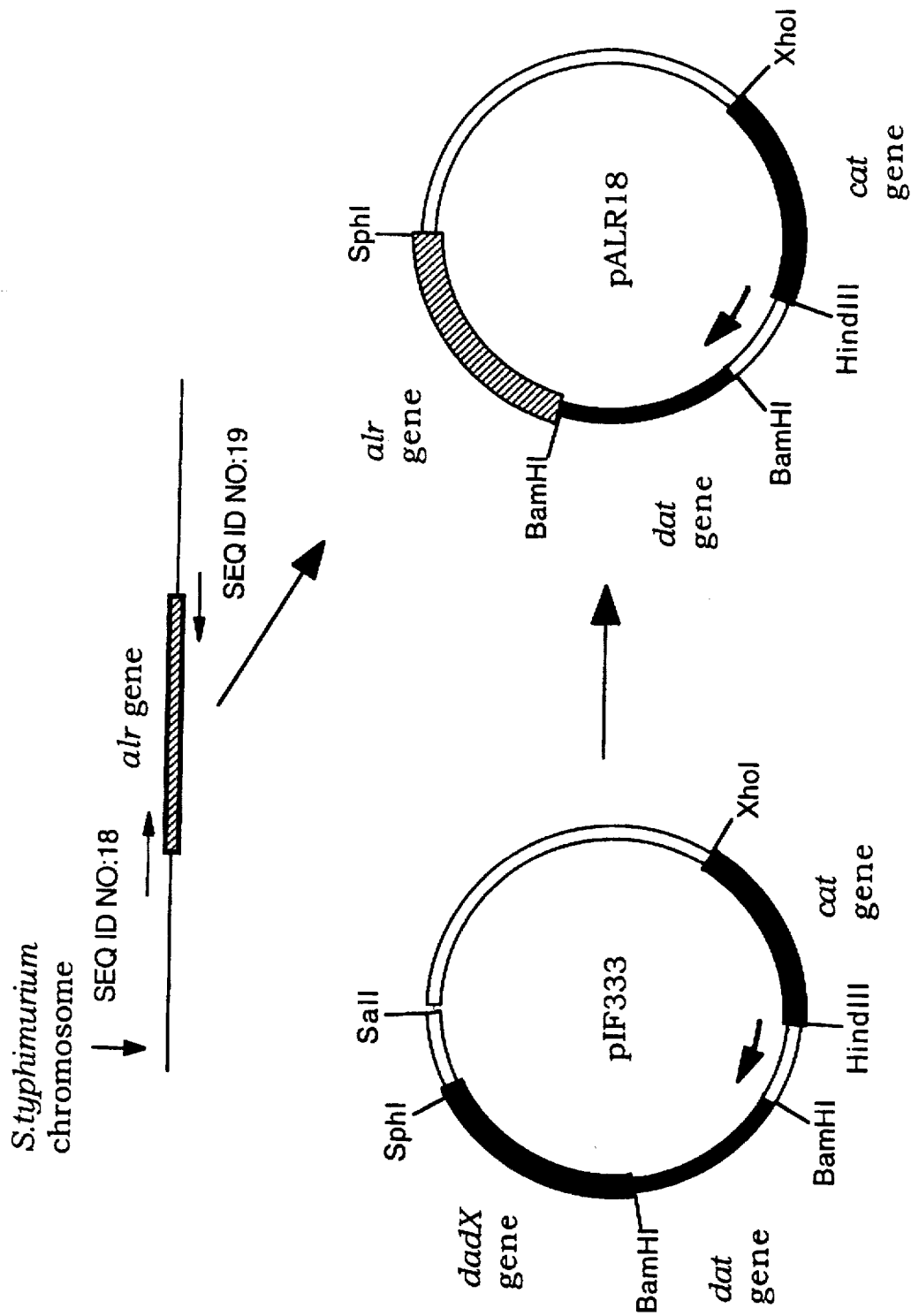
FIG. 11. is a schematic diagram showing construction of plasmid pALR18.

The 1098 bp PCR product was cleaved with BamHI and SphI yielding a 1082 BamHI to SphI fragment which was isolated using a QIAquick gel extraction kit (QIAGEN) following electrophoresis on a 1% agarose TBE gel. This fragment was then ligated to the 5.7 kB fragment of pIF333 to generate pALR18. Construction of pALR18 is shown in FIG. 11.

Example 6

ISOLATION OF THE L-AMINODEAMINASE GENE AND CONSTRUCTION OF THE pPT363 PLASMID

The L-aminodeaminase gene (lad) was isolated from the chromosome of a *Proteus myxofaciens* strain ATCC accession number 19692 using a PCR reaction carried out under standard conditions using an extension time of 2 minutes and the following oligonucleotides:

MB 2198:
5'TTTAGCGCATGCAAGGAGGATCAACTAT-GAACATTTCAAGGAGAAAG 3' (SEQ ID NO: 20)

MB2201:
5'AGCTTTGTCGACGGGCCCTTACT-
TAAAACGATCCAAAC 3' (SEQ ID NO: 21)

Figure 12:
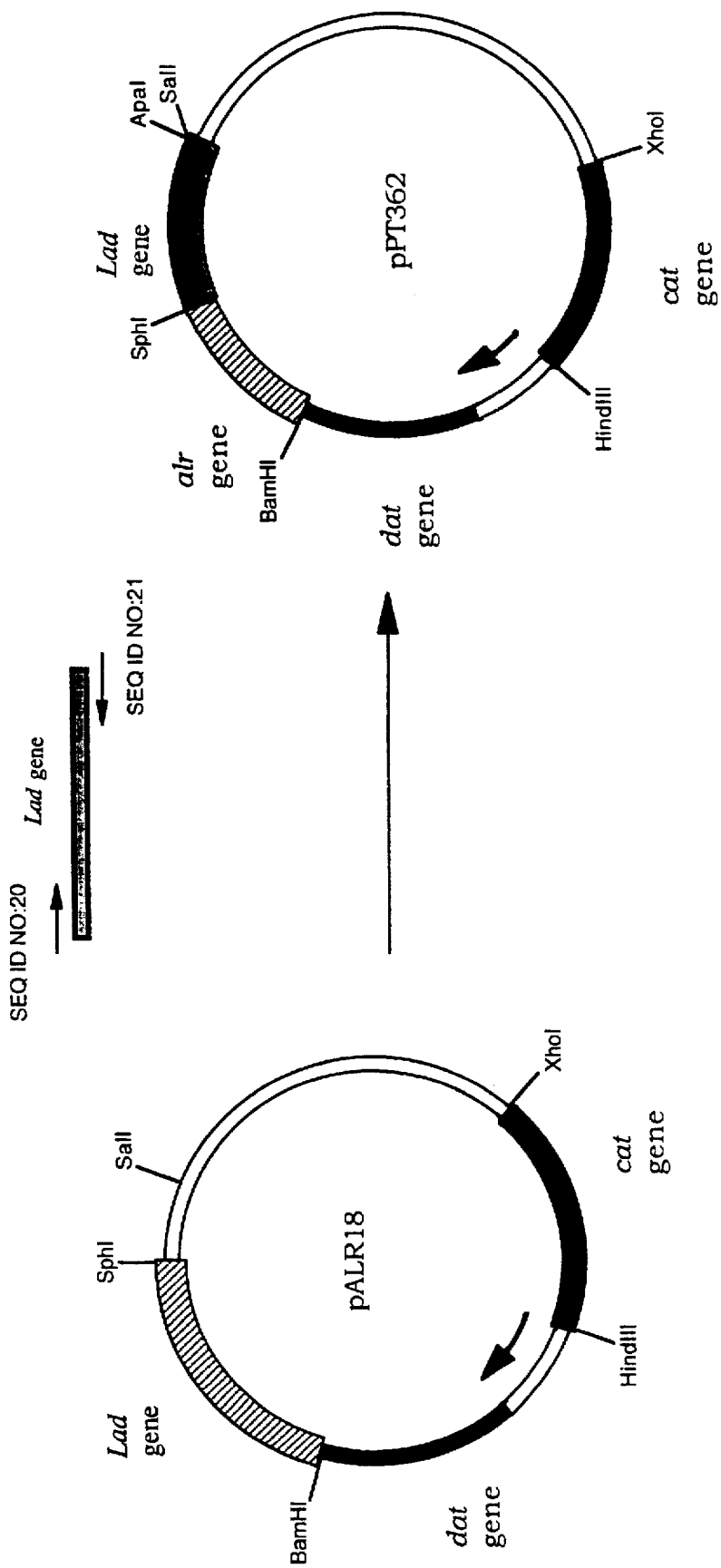
FIG. 12. is a schematic diagram showing construction of plasmid pPT362.

The fragment was cleaved by the enzymes SphI and SalI and ligated to the 6.84 kb fragment of pALR18 produced form similar cleavage. The resulting plasmid was named pPT362. Construction of pPT362 is shown in FIG. 12.

Figure 13:
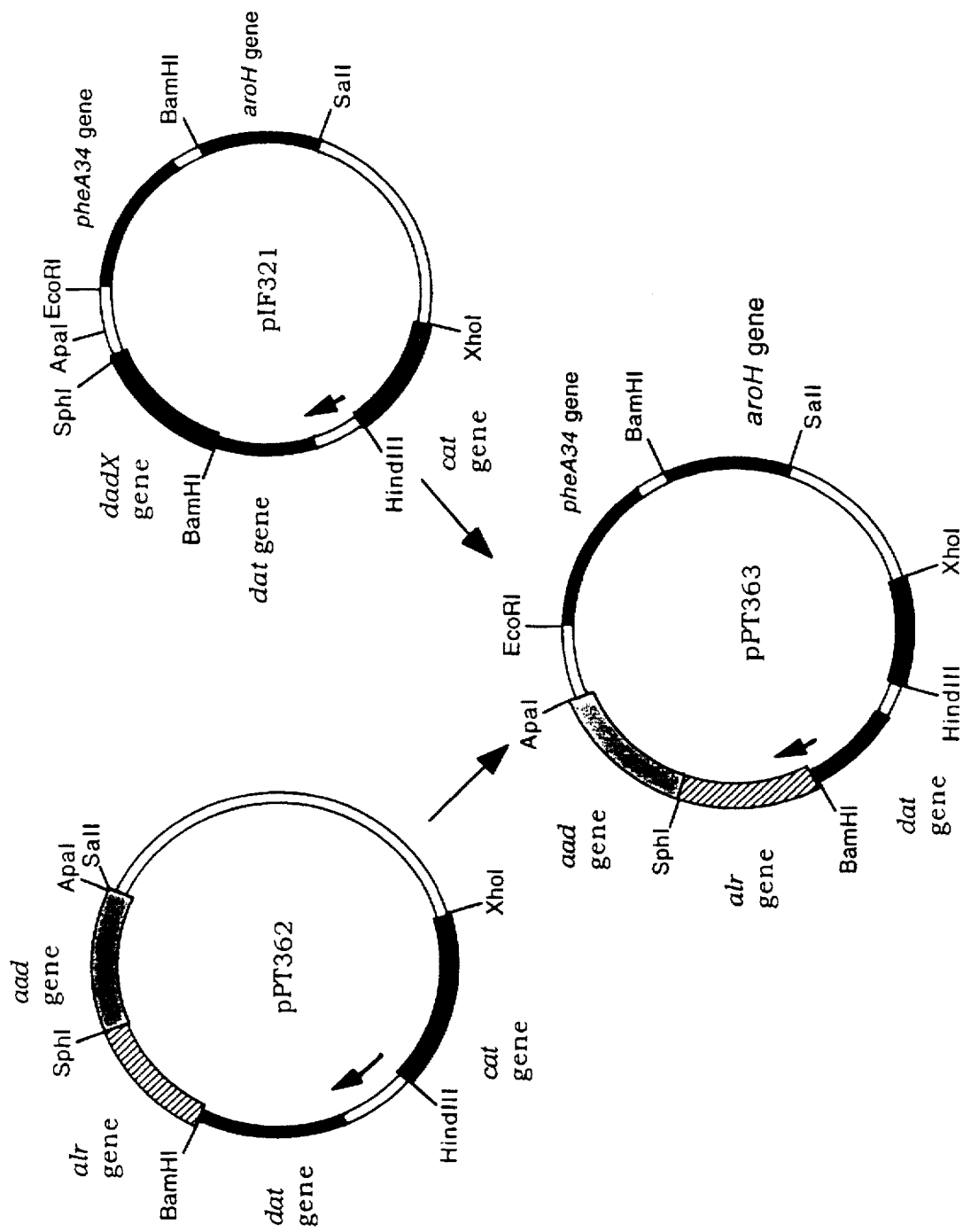
FIG. 13. is a schematic diagram showing construction of plasmid pPT363.

Plasmid pPT363 was generated from pPT362 and plasmid pIF321. Both pPT362 and pIF321 were cleaved with XhoI and ApaI. The 4.67 kB fragment of pPT362 and the 7.49 kB fragment of pIF321 were isolated and ligated to generate pPT363. Construction of pPT363 is shown in FIG. 13.

Example 7

CONSTRUCTION OF THE STRAIN IF3

The *Escherichia coli* strain pIF3 was derived from RY347 (ATCC Accession Number 69766). RY347 was transduced to tyrB+ using standard P1 transducing methodology as described in Miller et al., *A Short Course in Bacterial Genetics*, incorporated by reference herein. The selection for tyrB+ transductants was the loss of tyrosine auxotrophy, similarly the strain was transduced to ilvE+ selecting for loss of isoleucine auxotrophy. The resulting isolate was designated pIF3.

Example 8

FERMENTATION PROCESS FOR THE PRODUCTION OF D-PHENYLALANINE WITHOUT THE ADDITION OF AN EXTERNAL AMINO DONOR

The strain IF3 was transformed with plasmids pPT363 and pIF1003. The transformed IF3 strain was used to inoculate a 2800 ml Fernbach flask containing 1 L of the following growth medium:

| Potassium Phosphate (dibasic) | 13 g |
| --- | --- |
| Potassium Phosphate (monobasic) | 2 g |
| Ammonium Phosphate | 4 g |
| Ferric Ammonium Citrate | 0.24 g |
| Yeast Extract | 2 g |
| Magnesium Sulphate (7 * $H_2O$) | 1 g |
| Water | 930 mls |

The strain was grown to 800–900 Klett Units and used to inoculate the fermentor. The fermentor was a Biolaffite 78-100 (St Germain-en Laye, France) 20 L. The following are the conditions under which the fermentor was operated.

| Agitation | 500 rpm |
| --- | --- |
| Temperature | 32° C. |
| Backpressure | 0.7 Bar |
| pH | 7.2 with 50% KOH |
| Aeration | 1 vvm |
| Set Volume | 10 L |
| Inoculation | 1 L |
| Run Time | 67 hrs |

The fermentation medium used is listed in the following table.

| Magnesium Sulphate (7 * $H_2O$) | 5.35 g/l |
| --- | --- |
| Ferric Ammonium Citrate | 0.3 g/l |
| Potassium Phosphate (Dibasic) | 4.6 g/l |
| Manganese Sulphate | 0.023 g/l |
| Antifoam (Mazur Mazu) DF204 | 0.4 ml |
| $(NH_4)_2HPO_4$ | 21 g/l |
| Yeast Extract | 5 g/l |
| L-alanine | 1 g/l |

During the fermentation process glucose was fed at a variable rate to achieve a concentration of 10–15 g/l for the first 12 hrs then less than 1 g/l for the remaining time for a total of 1204 g in 48 hours. The fermentation resulted in 1.12 g/l of D-phenylalanine and 0.47 g/l of L-phenylalanine being produced.

Example 9

FERMENTATION PROCESS FOR THE PRODUCTION OF D-PHENYLALANINE WITH THE ADDITION OF D-, L-ALANINE FEED AS AN AMINO DONOR

The fermentation process for Example 9 was identical to the fermentation process in Example 8, except for the following aspects. The total glucose fed was 1976 g over 48 hours. The yeast extract was used at 2 g/l. The fermentation medium included a D-, L-alanine feed whereby a total of 1400 mls of 167 g/l D-, L-alanine was fed at a rate of 1.9 ml/min starting 12 hrs from the beginning of the fermentation. The fermentation resulted in 4.15 g/l of D-phenylalanine and 0 g/l of L-phenylalanine being produced.

Example 10

FERMENTATION PROCESS FOR THE PRODUCTION OF D-PHENYLALANINE WITH THE ADDITION OF D-, L-ALANINE AS AN AMINO DONOR AND L-PHENYLALANINE AS A KETO ACID PRECURSOR

The fermentation process for Example 10 was identical to Example 8 except for the following aspects. The growth medium used in the fermentation is listed in the following table:

| Magnesium Sulphate (7 * $H_2O$) | 8.03 g/l |
| --- | --- |
| Ferric Ammonium Citrate | 0.195 g/l |
| Potassium Phosphate (Dibasic) | 6.9 g/l |
| Manganese Sulphate | 0.0345 g/l |
| Antifoam (Mazur Mazu) DF204 | 0.6 ml |
| $(NH_4)_2HPO_4$ | 31.5 g/l |
| Yeast Extract | 7.5 g/l |
| L-alanine | 1.5 g/l |

The amount of glucose fed was 2021 g over 52 hours. The fermentation medium included a D-, L-alanine feed whereby a total of 1400 mls of 167 g/l D-, L-alanine was fed at a rate of 1.9 ml/min starting 12 hrs from the beginning of the fermentation. In addition, L-phenylalanine was fed at the same concentration and rate as the D-, L-alanine. The fermentation resulted in 13.66 g/l of D-phenylalanine and 0.87 g/l L-phenylalanine being produced.

Example 11

CONSTRUCTION OF PLASMID pPT361

Plasmid pPT361 was derived from pIF306 as follows. pIF306 was cleaved with the enzymes BamHI and SphI. The 3.9 kb fragment was isolated and ligated to a similarly cleaved fragment containing the *Escherichia coli* K12 ilvE gene which was generated by PCR from W3110 chromosome using the following oligonucleotide primers:

5' CGC GGA TCC ACT ATG ACC ACG AAG AAA GCT GAT TAC ATT TGG 3' (SEQ ID NO: 22)

5' CAG CGT GCA TGC TTA TTG ATT AAC TTG ATC TAA CCA GC 3' (SEQ ID NO: 23)

The resulting vector was named pIF307. Plasmid pIF307 was cleaved with enzymes EcoRI and PstI and the 4.1 kB fragment isolated. This was ligated to a similarly cleaved and purified 982 bp DNA fragment containing the kanamycin resistance gene from pLG338. This was generated using PCR with the following oligonucleotide primers:

5' CCG GAA TTC ACG TTG TGT CTC AAA ATC TCT GAT 3' (SEQ ID NO: 24)

5' CCG CTG CAG GCC GTC CCG TCA AGT CAG CGT AAT G 3' (SEQ ID NO: 25)

The resulting plasmid cleaved was named pIF312. Plasmid pIF12 was cleaved by EcoRI and BamHI and ligated to the phage lambda C1857 gene which was similarly cleaved following isolation by PCR using the Lambda ZapII vector (Stragene, La Jolla, Calif.) as template and the following oligonucleotide primers:

5' TTTGGATCCTCCTTAGTACATGCAACC 3' (SEQ ID NO: 26)

5' TTTGAATTCGGATGAAGATTCTTGCTCGATTGT 3' (SEQ ID NO: 27)

The resulting plasmid was named pPT353. This plasmid was then cleaved with PstI and EagI and the 3.17 kb fragment was isolated. This was ligated to the similarly cleaved 2.5 kb fragment generated by similar cleavage of pIF1003. The resulting vector was named 4.7 kb fragment isolated. This was ligated to the following oligonucleotide linker 5' GATCCTAGGTACCGGTGCGGCCGCATGCTGACTGACTGAAGATCCCGGGCGATTCTACGCCCGGGTTTTTTATG 3' (SEQ ID NO: 28)

5' TCGACATAAAAAACCCGGGCGTAGAATCGCCCGGGATCTTCAGTCAGTCAGCATGCGGCCGCACCGGTACCTAG 3' (SEQ ID NO: 29)

The resulting plasmid was named pPOT2. This plasmid was cleaved with XhoI and PstI and the 3.9 kb fragment isolated. This was ligated to a fragment containing the chloramphenicol resistance gene which was isolated bay PCR using pIF319 plasmid DNA as template and the following oligonucleotide primers.

5' GAC CTC GAG GCA CTT TGC GCC GAA TAA ATA CCT GTG 3' (SEQ ID NO: 30)

5' GAC CTG CAG CAC CAG GCG TTT AAG GGC ACC AAT AAC 3' (SEQ ID NO: 31)

The resulting plasmid was named pPOT3. This was cleaved with BamHI and SphI. The 4.8 bp fragment was isolated and ligated to similarly cleaved fragment containing the *Proteus myxofaciens* Lad gene. This was isolated by PCR from the chromosome from ATCC 19692 using the following oligonucleotide primers:

5' TTTGGATCCAAGATGAACATTTCAAGGAGAAAG 3' (SEQ ID NO: 32)

5' AGCTTTGTCGACGCATGCTTACTTCTTAAAACGATCCAAAC 3' (SEQ ID NO: 33)

Example 12

DETERMINATION OF Lad AMINO ACID SUBSTRATES

Each of the amino acid substrates listed in Table 1 were determined to be a suitable substrate for the Lad enzyme using the following thin layer chromatography (TLC) Lad assay. All of the chemicals used were obtained from Sigma Chemical Company, St. Louis, Mo.

The assay mix contained 10 mg/ml of one of the amino acid substrates listed in Table 1 and 100 mM Tris HCl with a pH of 7.5. The assay mix (2 mls) was added to 100 mg of cell pellet from Strain W3110 containing plasmid pPT361 which contained the Lad gene.

Cells were prepared from overnight culture of 200 mls of LB medium (Difco, Detroit, Mich.) at 37° C. in 1 L shake flasks. Cells were washed once in 100 mM tris HCL pH 7.5 and pelleted by centrifugation. The reaction was carried out for 16 hours at 37° C. 0.005 ml of reaction mix was spotted on Silica TLC plates #60 F-254 (EM Science Cincinnati Ohio).

The chromatography was carried out using the following solvent: water (40%); methanol (40%); and acetonitrile (20%). The TLC plates were air dried and sprayed with 2% Ninhydrin in ethanol and then baked for 10 minutes.

The conversion of each of the amino acids listed in Table 1 to their corresponding keto acids was determined by the absence of the amino acid derived spots against co-chromatographed known standards. Each of the amino acid substrates listed in Table 1 were found to be suitable substrates for the Lad enzyme.

Example 13

DETERMINATION OF Dat KETO ACID SUBSTRATES

The Dat enzyme was assayed with each keto acid substrate listed in Table 1 in a coupled enzyme assay under the following conditions. All of the chemicals used were obtained from Sigma Chemical Company, St. Louis, Mo.

The assay mix contained 500 u/ml Dat; 30 mM D-Alanine; 30 mM Keto Acid Substrate; 0.2 mM NADH; and 100 mM Tris-HCl. The pH of the assay mixture was 8.3. The assay was carried out using 1 ml of solution containing 0.85 ml of assay mix, 0.05 ml of D-Lactate and 0.1 ml of W3110 cells (ATCC27325) containing plasmid pIF1003 at an $O.D._{650}$ of 0.5–1.0.

Cells were prepared from overnight culture in 200 mls of LB medium (Difco, Detroit, Mich.) at 37° C. in 1 L shake flasks. Cells were washed once in 100 mM Tris HCl pH 7.5, centrifuged and taken up in water. The reaction for each of the keto acid substrates in Table 1 was monitored by measuring $\Delta A_{340}$ at 37° C. Each of the keto acid substrates assay in Table 1 were found to be suitable substrates for the Dat enzyme.

What is claimed is:

1. A method for producing a D-amino acid in a cell, comprising:
   (a) incorporating into the cell a D-aminotransferase gene and a L-aminodeaminase gene;
   (b) culturing the cell in a cell culture medium;
   (c) and isolating the D-amino acid from the cell culture medium.

2. The method of claim 1, further comprising the step of introducing a D-aminodeaminase gene mutation into the cell such that the D-aminodeaminase gene is nonfunctional.

3. The method of claim 1, wherein the cell is a bacterial cell.

4. The method of claim 2, wherein the bacterial cell is selected from the group consisting of *Bacillus subtilis*, *Bacillus sphaericus*, *Bacillus stearothermophilus*, Pseudomonas, Klebsiella, Salmonella, Brevibacterium, Micrococcus, Corynebacterium and *Escherichia coli*.

5. The method of claim 4, wherein the cell is a *Escherichia coli*.

6. The method of claim 5, further comprising the step of introducing a dadA gene mutation into the *Escherichia coli* cell such that the dadA gene is nonfunctional.

7. The method of claim 1, wherein the D-aminotransferase gene is a *Bacillus sphaericus* D-aminotransferase gene.

8. The method of claim 1, wherein the L-aminodeaminase gene is a *Proteus myxofaciens* L-aminodeaminase gene or a *Proteus mirabilis* L-aminodeaminase gene.

9. The method of claim 1, further comprising the step of incorporating into the cell a racemase gene.

10. The method of claim 9, wherein the racemase gene is selected from the group consisting of alanine racemase, glutamate racemase, aspartate racemase and phenylalanine racemase.

11. The method of claim 10, wherein the racemase gene is alanine racemase.

12. The method of claim 1, wherein the D-amino acid is a natural or unnatural D-amino acid.

13. The method of claim 12, wherein the natural or unnatural D-amino acid is selected from the group consisting of isoleucine, leucine, tryptophan, tyrosine, valine, arginine, asparagine, glutamine, methionine, ornithine, serine, norleucine, norvaline, phenylalanine, dihydroxyphenylalanine, citrulline, cysteine, histidine and lysine.

14. The method of claim 13, wherein the natural D-amino acid is phenylalanine.

15. The method of claim 1, wherein the culture medium contains an amino donor.

16. The method of claim 15, wherein the amino donor is selected from the group consisting of L-alanine, L-glutamate, L-phenylalanine, L-aspartate and a racemic mixture one of the aforementioned L-amino acids.

17. The method of claim 16, wherein the amino donor racemic mixture is aspartate.

18. The method of claim 1, wherein the culture medium contains an L-amino acid substrate.

19. The method of claim 18, wherein the L-amino acid substrate is selected from the group consisting of isoleucine, leucine, tryptophan, tyrosine, valine, arginine, asparagine, glutamine, methionine, ornithine, serine, norleucine, norvaline, phenylalanine, dihydroxyphenylalanine, citrulline, cysteine, histidine and lysine.

20. A method for the preparation of a substantially pure D-amino acid in a cell, comprising:
   (a) incorporating into the cell a D-aminotransferase gene and a L-aminodeaminase gene;
   (b) culturing the cell in a cell culture medium; and
   (c) isolating the substantially pure D-amino acid from the cell culture medium.

21. The method of claim 20, wherein the D-amino acid is produced in high yields.

22. The method of claim 1, wherein the D-aminotransferase gene and the L-aminodeaminase gene are incorporated into the cell using a plasmid.

23. A method for producing D-phenylalanine in a cell, comprising:
   (a) incorporating into the cell a D-aminotransferase gene, a L-aminodeaminase gene and means for increasing production of phenylpyruvic acid;
   (b) culturing the cell in a cell culture medium; and
   (c) isolating the D-phenylalanine from the cell culture medium.

24. The method of claim 23, further comprising the step of introducing a D-aminodeaminase gene mutation into the cell such that the D-aminodeaminase gene is nonfunctional.

25. The method of claim 23, wherein the cell is a bacterial cell.

26. The method of claim 25, wherein the bacterial cell is selected from the group consisting of *Bacillus subtilis*, *Bacillus sphaericus*, *Bacillus stearothermophilus*, Pseudomonas, Klebsiella, Salmonella, Brevibacterium, Micrococcus, Corynebacterium and *Escherichia coli*.

27. The method of claim 26, wherein the cell is a *Escherichia coli*.

28. The method of claim 27, further comprising the step of introducing a dadA gene mutation into the *Escherichia coli* cell such that the dadA gene is nonfunctional.

29. The method of claim 23, wherein the D-aminotransferase gene is a *Bacillus sphaericus* D-aminotransferase gene.

30. The method of claim 23, wherein the L-aminodeaminase gene is a *Proteus myxofaciens*

L-aminodeaminase gene or a *Proteus mirabilis* L-aminodeaminase gene.

31. The method of claim 23, further comprising the step of incorporating into the cell a racemase gene.

32. The method of claim 31, wherein the racemase gene is selected from the group consisting of alanine racemase, glutamate racemase, aspartate racemase or phenylalanine racemase.

33. The method of claim 32, wherein the racemase gene is alanine racemase.

34. The method of claim 23, wherein the culture medium contains an amino donor.

35. The method of claim 34, wherein the amino donor is selected from the group consisting of L-alanine, L-glutamate, L-phenylalanine, L-aspartate and a racemic mixture one of the aforementioned L-amino acids.

36. The method of claim 35, wherein the racemic mixture is aspartate.

37. The method of claim 23, wherein the culture medium contains L-phenylalanine as a substrate.

38. The method of claim 23, wherein means for increasing production of phenylpyruvate comprises incorporating into the cell an aroH gene.

39. The method of claim 23, wherein means for increasing production of phenylpyruvate comprises incorporating into the cell a pheA gene.

40. A method for the preparation of a substantially pure D-phenylalanine acid using a culture of the cell of claim 23.

41. A method for the preparation of substantially pure D-phenylalanine in a cell, comprising:

(a) incorporating into the cell a D-aminotransferase gene and a L-aminodeaminase gene;

(b) culturing the cell in a cell culture medium; and (c) isolating the substantially pure D-phenylalanine from the cell culture medium.

42. The method of claim 41, wherein the D-aminotransferase gene and the L-aminodeaminase gene are incorporated into the cell using a plasmid.

43. A recombinant cell, comprising an exogenous D-aminotransferase gene and an exogenous L-aminodeaminase gene.

44. The recombinant cell of claim 43, further comprising a D-aminodeaminase gene mutation in the cell such that the D-aminodeaminase gene is nonfunctional.

45. The recombinant cell of claim 43, wherein the exogenous D-aminotransferase gene is a *Bacillus sphaericus* D-aminotransferase gene.

46. The recombinant cell of claim 43, wherein the exogenous L-aminodeaminase gene is a *Proteus myxofaciens* L-aminodeaminase gene or a *Proteus mirabilis* L-aminodeaminase gene.

47. The recombinant cell of claim 43, further comprising an exogenous racemase gene.

48. The recombinant cell of claim 47, wherein the exogenous racemase gene is a *Salmonella typhimurium* gene.

49. The recombinant cell of claim 48, wherein the *Salmonella typhimurium* gene is alanine racemase.

50. The recombinant cell of claim 43, further comprising an exogenous aroH gene and an exogenous pheA gene.

* * * * *

UNITED STATES PATENT AND TRADEMARK OFFICE
CERTIFICATE OF CORRECTION

PATENT NO. : 5,728,555

DATED : March 17, 1998

INVENTOR(S) : IAN G. FOTHERINGHAM ET AL.

It is certified that error appears in the above-identified patent and that said Letters Patent is hereby corrected as shown below:

Title page,
AT [56] REFERENCES CITED

OTHER PUBLICATIONS

"Amintransferases," vol. 264," should read
--Aminotransferases," vol. 264,--.

COLUMN 2

Line 12, "Bacillus sphaeri-" should read
--*Bacillus sphaericus*--; and
Line 13, "cus" should be deleted.

COLUMN 6

Line 5, "obtained" should read --obtained from--; and
Line 40, "protein" should read --protein.--.

COLUMN 10

Line 4, "see" should read --(see--.

COLUMN 36

Line 17, "one" should read --of one--.

UNITED STATES PATENT AND TRADEMARK OFFICE
CERTIFICATE OF CORRECTION

PATENT NO. : 5,728,555

DATED : March 17, 1998

INVENTOR(S) : IAN G. FOTHERINGHAM ET AL.     Page 2 of 2

It is certified that error appears in the above-identified patent and that said Letters Patent is hereby corrected as shown below:

<u>COLUMN 37</u>

Line 16, "one" should read --of one--.

Signed and Sealed this

Seventeenth Day of November, 1998

Attest:

BRUCE LEHMAN

*Attesting Officer*     Commissioner of Patents and Trademarks